US009717655B2

(12) United States Patent
Nova et al.

(10) Patent No.: US 9,717,655 B2
(45) Date of Patent: Aug. 1, 2017

(54) ELECTRONIC PILL BOX WITH DETACHABLE DAY MODULE WHICH USES A BLISTER PACK

(71) Applicant: Next Paradigm Inc., Toronto (CA)

(72) Inventors: Edward Nova, Thornhill (CA); Ajay Majithia, Brampton (CA); Ami Majithia, Brampton (CA); Robert G. Dickie, King City (CA); Walter Prokopchuk, King City (CA)

(73) Assignee: Next Paradigm Inc., Toronto, Ontario (CA)

( * ) Notice: Subject to any disclaimer, the term of this patent is extended or adjusted under 35 U.S.C. 154(b) by 0 days.

(21) Appl. No.: 15/042,688

(22) Filed: Feb. 12, 2016

(65) Prior Publication Data

US 2016/0158109 A1    Jun. 9, 2016

Related U.S. Application Data

(63) Continuation-in-part of application No. 14/858,041, filed on Sep. 18, 2015, which is a continuation-in-part of application No. 13/965,966, filed on Aug. 13, 2013, now Pat. No. 9,311,452.

(51) Int. Cl.
| | |
|---|---|
| *G08B 21/00* | (2006.01) |
| *A61J 7/04* | (2006.01) |
| *A61J 1/03* | (2006.01) |
| *A61J 7/00* | (2006.01) |
| *G06F 19/00* | (2011.01) |

(52) U.S. Cl.
CPC ............ *A61J 7/0481* (2013.01); *A61J 1/035* (2013.01); *A61J 7/0084* (2013.01); *A61J 7/0418* (2015.05); *A61J 7/0436* (2015.05); *G06F 19/3462* (2013.01); *A61J 2200/30* (2013.01); *A61J 2205/20* (2013.01)

(58) Field of Classification Search
CPC ..................................... A61J 7/0481
USPC ................... 340/309.16, 573.1, 539.12
See application file for complete search history.

(56) References Cited

U.S. PATENT DOCUMENTS

| | | | |
|---|---|---|---|
| 3,762,601 | A | 10/1973 | McLaughlin |
| 4,275,384 | A | 6/1981 | Hicks et al. |
| 4,382,688 | A | 5/1983 | Machamer |

(Continued)

FOREIGN PATENT DOCUMENTS

| | | |
|---|---|---|
| CN | 103315909 | 9/2013 |
| FR | 2892016 | 4/2007 |

(Continued)

*Primary Examiner* — Jeffery Hofsass
(74) *Attorney, Agent, or Firm* — Sand & Sebolt

(57) ABSTRACT

An electronic pill box for receiving a blister pack having a plurality of dosettes pre-loaded with doses of medication. The pill box includes a base module having a plurality of receptacles that receive the dosettes of the blister pack. The number of receptacles is sufficient to hold about a month of medication. A day module is engaged with the base module but is detachable therefrom. Individual dosettes are detached from the blister pack and loaded into receptacles in the day module. The base module and day module include capacitance sensors for determining if a dose of medication has been removed at the required time. The day module also includes a light sensor assembly that verifies whether the dosettes loaded into the day module's receptacles are the correct dosettes for the time of day a particular dose of medication should be taken.

20 Claims, 21 Drawing Sheets

(56) References Cited

U.S. PATENT DOCUMENTS

| | | | |
|---|---|---|---|
| 4,748,600 | A | 5/1988 | Urquhart |
| 5,020,037 | A | 5/1991 | Raven |
| 5,099,463 | A | 3/1992 | Lloyd et al. |
| 5,200,891 | A | 4/1993 | Kehr et al. |
| 5,850,937 | A | 12/1998 | Rauche |
| 6,048,087 | A | 4/2000 | Laurent et al. |
| 2003/0080854 | A1 | 5/2003 | Brakus |
| 2005/0075908 | A1 | 4/2005 | Stevens |
| 2010/0314282 | A1 | 12/2010 | Bowers |
| 2011/0155602 | A1 | 6/2011 | Sterry et al. |
| 2012/0006708 | A1 | 1/2012 | Mazur |
| 2013/0222135 | A1 | 8/2013 | Stein et al. |

FOREIGN PATENT DOCUMENTS

| | | |
|---|---|---|
| WO | 0217850 | 3/2002 |
| WO | 2012111034 | 8/2012 |
| WO | 2013071225 | 5/2013 |

ELECTRONIC PILL BOX WITH DETACHABLE DAY MODULE WHICH USES A BLISTER PACK

CROSS-REFERENCE TO RELATED APPLICATIONS

This is a Continuation-in-Part of U.S. patent application Ser. No. 14/858,041 filed Sep. 19, 2015, which is a Continuation-in-Part of U.S. patent application Ser. No. 13/965,966, filed Aug. 13, 2013, the entire disclosures of which are incorporated herein by reference.

BACKGROUND OF THE INVENTION

Technical Field

This invention relates generally to pill boxes useful for storing medication. More particularly, this invention relates to a pill box having an electronic reminder system. Specifically, this invention is directed to an electronic pill box comprising a base module and a selectively detachable day module; each module including touch-free capacitance sensors for determining whether medication has been removed therefrom; and including a light sensing assembly for determining whether the correct medication has been loaded into the day module.

Background Information

Doctors prescribe medication for patients suffering from a variety of illnesses. An issue that is fairly common is that patients frequently do not follow the exact dosage regimen prescribed by the physician. They will tend to forget to take a dose at a prescribed time or will accidently double up dosages when they can't remember if they took the medication at a prescribed time. Because the prescribed regimen is not being followed, the healing which should occur through action of the medication on their body may be slowed or the patient could actually put their health in jeopardy by overdosing themselves.

A number of electronic pill boxes have been proposed in the prior art including those disclosed in U.S. Pat. No. 3,762,601 (McLaughlin); U.S. Pat. No. 4,275,304 (Hicks); U.S. Pat. No. 4,302,688 (Machamer); U.S. Pat. No. 4,742,600 (Urquhart); U.S. Pat. No. 5,020,037 (Raven); U.S. Pat. No. 5,099,403 (Lloyd et al); U.S. Pat. No. 5,200,891 (Kehr et al); U.S. Pat. No. 5,850,937 (Rauche) and U.S. Pat. No. 6,042,087 (Laurent et al).

SUMMARY

One of the problems with prior art electronic pill box reminder systems is that actual pill box may be of too great a size for carrying around as a patient or caregiver performs their daily tasks. The device of the present invention is configured to address at least aspects of this problem.

An electronic pill box for receiving a blister pack having a plurality of dosettes pre-loaded with doses of medication. The pill box includes a base module having a plurality of receptacles that receive the dosettes of the blister pack. The number of receptacles is sufficient to hold about a month of medication. A day module is engaged with the base module but is detachable therefrom. Individual or single dosettes are detached from the blister pack and loaded into receptacles in the day module. The base module and day module include capacitance sensors for determining if a dose of medication has been removed at the required time. The day module also includes a light sensor assembly that verifies whether the dosettes loaded into the day module's receptacles are the correct dosettes for the time of day a particular dose of medication should be taken.

In one aspect, the invention may provide an electronic pill box comprising a base module adapted to hold a blister pack comprising a plurality of dosettes each pre-loaded with a quantity of medication; a day module engageable with the base module and being selectively disengageable therefrom, said day module being adapted to receive one or more dosettes detached from the blister pack; and a first electronic reminder system provided in the base module or the day module, said first electronic reminder system being operable to remind a patient to remove a dose of medication from the pill box at a pre-determined time. The pill box may further comprise a second electronic reminder system provided in the other of the base module or the day module; said second electronic reminder system being operable to remind a patient to remove a dose of medication from the pill box at a pre-determined time. The first electronic reminder system is operable in the base module and the second electronic reminder system is operable in the day module when the day module is disengaged from the base module.

In another aspect, the invention may provide a combination of an electronic pill box and a blister pack, where the electronic pill box comprises a base module having a first plurality of receptacles therein; a day module engageable with the base module and being selectively disengageable therefrom; said day module having a second plurality of receptacles therein, where the second plurality of receptacles is less than the first plurality of receptacles; a first electronic reminder system provided in the base module or the day module, said first electronic reminder system being operable to remind a patient to remove a dose of medication from the pill box at a pre-determined time; and the blister pack comprises a first plurality of dosettes joined together in side-by-side relationship, each dosette being pre-loaded with a dose of medication; and wherein the blister pack is removably engaged with the base module in such a way that each dosette is received within a different one of the first plurality of receptacles of the base module. The combination may further comprise a second plurality of dosettes that are separated from the blister pack and are each engaged in a different one of the second plurality of receptacles in the day module.

In another aspect the invention may provide a method of using an electronic pill box comprising providing an electronic pill box comprising a base module, a day module engageable with the base module and being selectively disengageable therefrom, a first electronic reminder system provided in the base module; a second electronic reminder system provided in the day module; and a blister pack pre-loaded with a plurality of doses of medication, each of said doses being retained in a dosette sealed by way of a colored film; detaching one or more individual dosettes from the blister pack; loading each detached dosette into a different one of a plurality of receptacles in the day module; activating a light source positioned adjacent each receptacle; causing light to travel along a first light pipe positioned proximate the light source; reflecting the light from the colored film of the dosette loaded into a particular receptacle; causing the reflected light to travel along a second light pipe; and detecting the color of the light from the second light pipe by way of a color sensor.

The method may further comprise linking the color sensor to a microcontroller provided in the day module or the base module; transferring data regarding the detected color of the light to the microcontroller; comparing, in the microcontroller, the detected color of the light with a set of predetermined colors to be associated with each of the receptacles in the day module. The method may further comprise issuing an alarm to the patient if the detected color of the light is different from the pre-determined color for a specific one of the receptacles.

BRIEF DESCRIPTION OF THE SEVERAL VIEWS OF THE DRAWINGS

A sample embodiment of the invention is set forth in the following description, is shown in the drawings and is particularly and distinctly pointed out and set forth in the appended claims.

Similar numbers refer to similar parts throughout the drawings.

DETAILED DESCRIPTION

Figure 10:
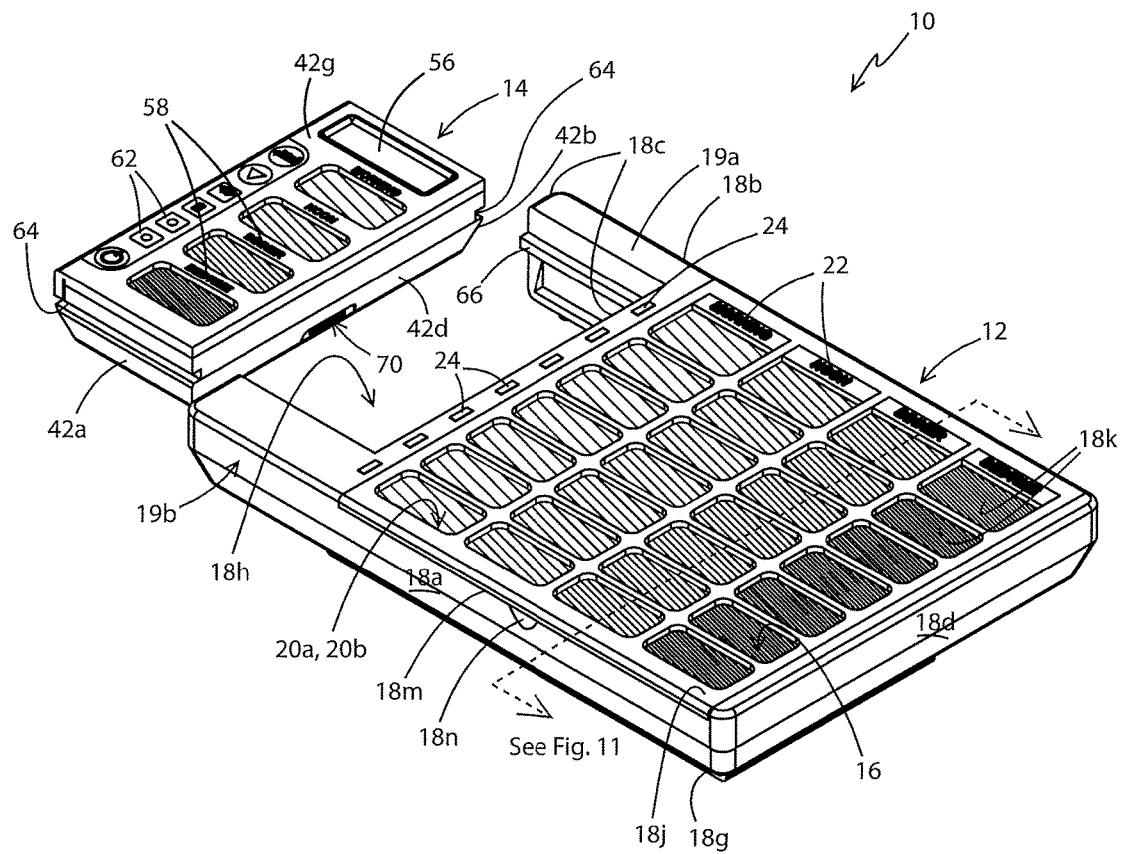
FIG. 10 is a right side top perspective view of the base module and day module disengaged from each other.
Figure 11:
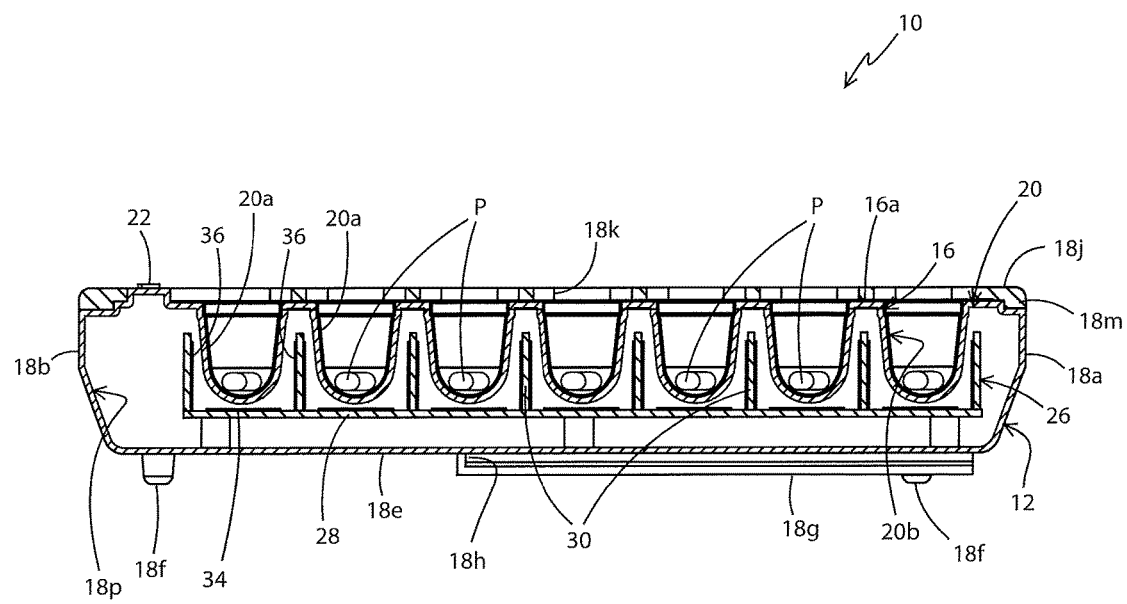
FIG. 11 is cross-section of the pill box taken along line 11-11 of FIG. 10.

Referring to FIGS. 1-21 there is shown an electronic pill box in accordance with an aspect of the present invention, generally indicated at 10. Pill box 10 comprises a base module 12 and a day module 14. Day module 14 is selectively engageable with base module 12 and is selectively detachable therefrom, as will later be described herein. Day module 14 is of a size that is suitable for carrying in a pocket or purse while base module 12 may be substantially larger than day module 14 and therefore more cumbersome to carry around on a daily basis. Base module 12 is configured to selectively receive and secure a blister pack 16 (FIG. 4) therein. Blister pack 16 is comprised of a plurality of individual dosettes 17 that are connected to each other (as will be described later herein). The dosettes 17 are preloaded with medication and the medication may be particularly prescribed for a specific patient. That medication may include pills "P" as illustrated in FIGS. 11 and 17. Day module 14 is configured to selectively receive a discrete number of individual dosettes 17 that have been detached from a portion of blister pack 16. The four dosettes 17 that are engageable with day module 14 may typically include enough medication for a single day. It will be understood that day module 14 may be slightly increased in size to include more than one day's medication but remain of a small enough size to be easily carried around. This slightly larger version of day module 14 is not illustrated herein.

Figure 7:
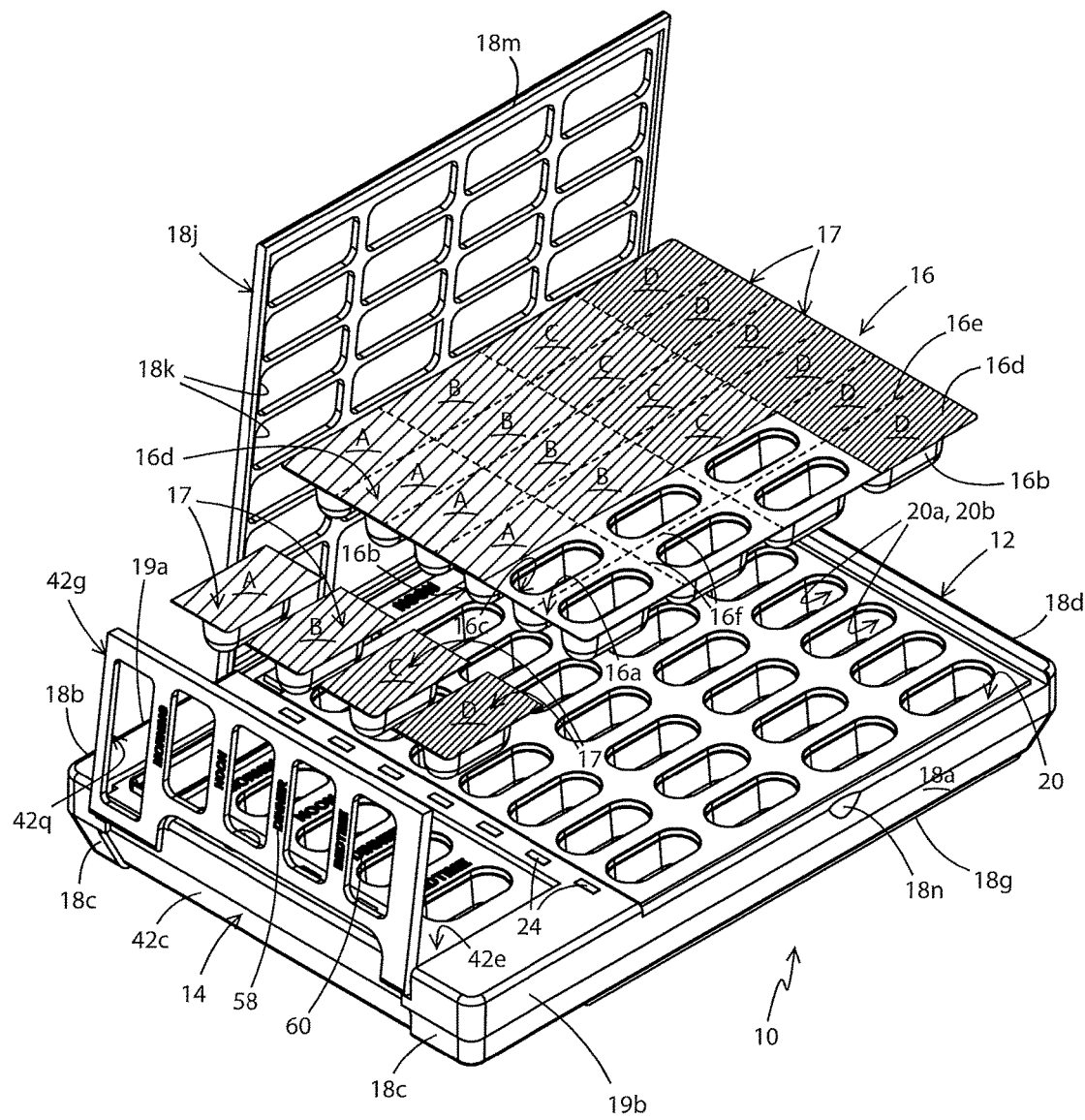
FIG. 7 is a top perspective view of the pill box of FIG. 6 showing four individual dosettes separated from the blister pack and positioned for insertion into the day module.
Figure 8:
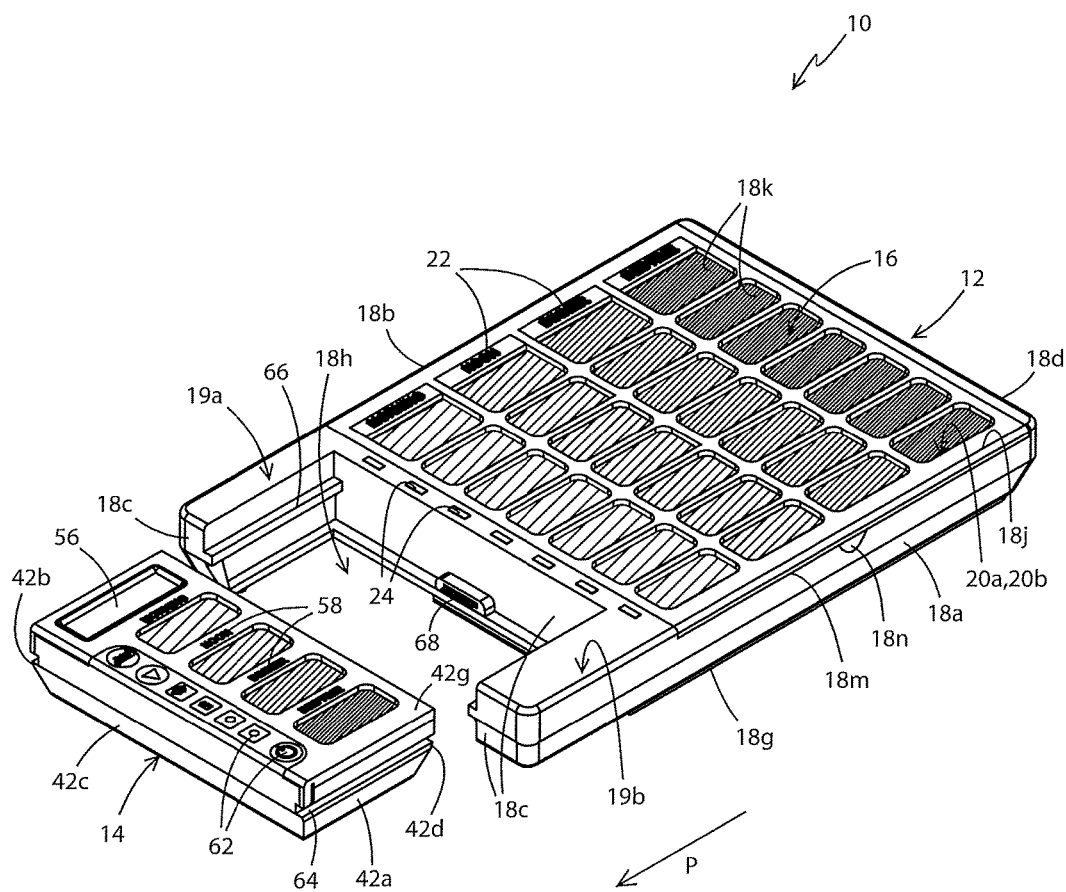
FIG. 8 is a left side top perspective view of the electronic pill box showing the day module disengaged from the base module.
Figure 9:
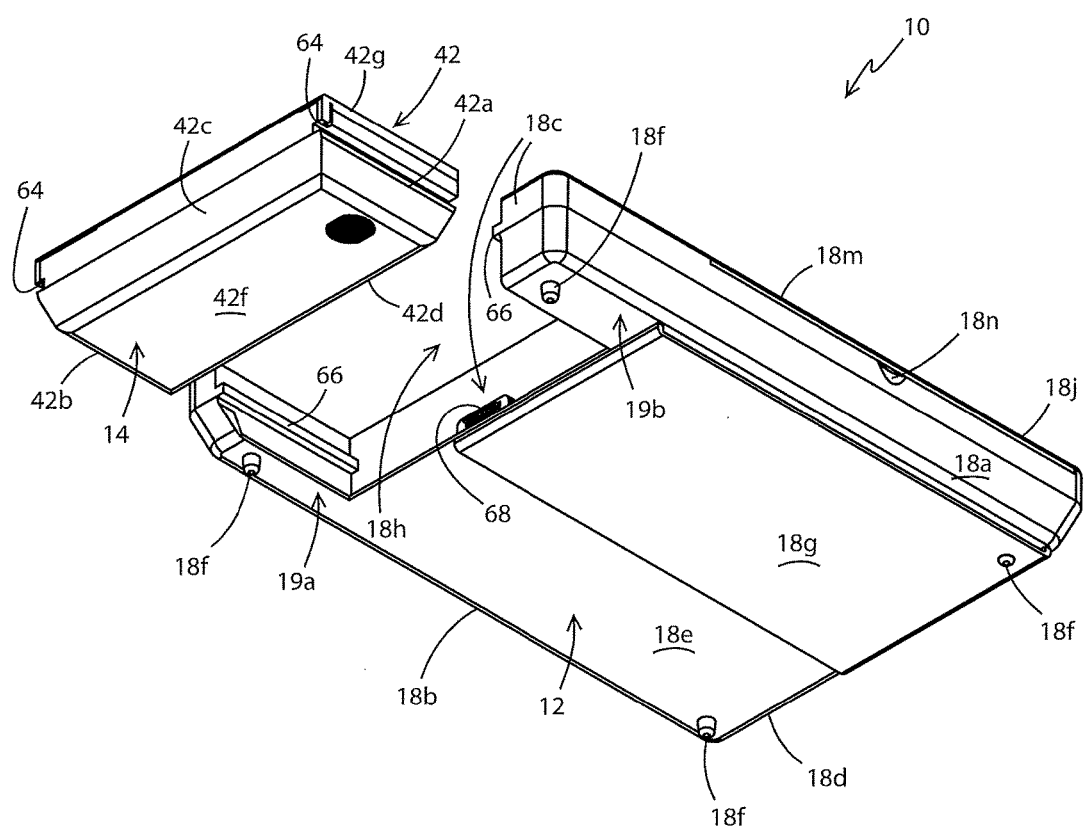
FIG. 9 is a bottom perspective view of the base module and day module as illustrated in FIG. 8.

Referring to FIGS. 1-9, base module 12 may comprise a housing 18 having a front wall 18a, a rear wall 18b (FIG. 2), a first side wall 18c (FIG. 8), a second side wall 18d and a bottom wall 18e (FIG. 9). Legs 18f (FIG. 3) may extend downwardly from bottom wall 18e so that base module 12 may be readily supported on a flat surface such as a bedside table. A frame 18g may also be provided on bottom wall 18e. A slot 18h may be defined between an interior surface of frame 18g and bottom wall 18e of housing 18. Slot 18h may be suitable for receiving one or more sheets/cards of information that may be provided with blister pack 16 or which may be received by the patient or a caregiver from a prescribing doctor.

The terms "user", "patient" and "caregiver" used herein should be understood to be interchangeable and used to refer to any person who requires or has access to pill box 10 and/or may be electronically, wirelessly or otherwise linked to pill box 10 for alert or compliance purposes; and who is authorized to load medication or remove medication from pill box 10.

FIG. 8 shows that base module 12 includes a first arm 19a and a second arm 19b that extend outwardly away from a top region and a bottom region of first side wall 18c. First and second arms 19a, 19b are spaced laterally apart from each other and are oriented generally parallel to each other. First and second arms 19a, 19b includes regions of first side wall 18c at their outermost ends as is shown in FIG. 9. First and second arms 19a, 19b and the region of first side wall 18c bound and define a recess 18h (best seen in FIGS. 8-10) that is complementary shaped and sized to receive and engage day module 14 therein. Day module 14 is captured between first arm 19a and second arm 19b and is interlockingly engaged therewith as will be later described herein.

Figure 1:
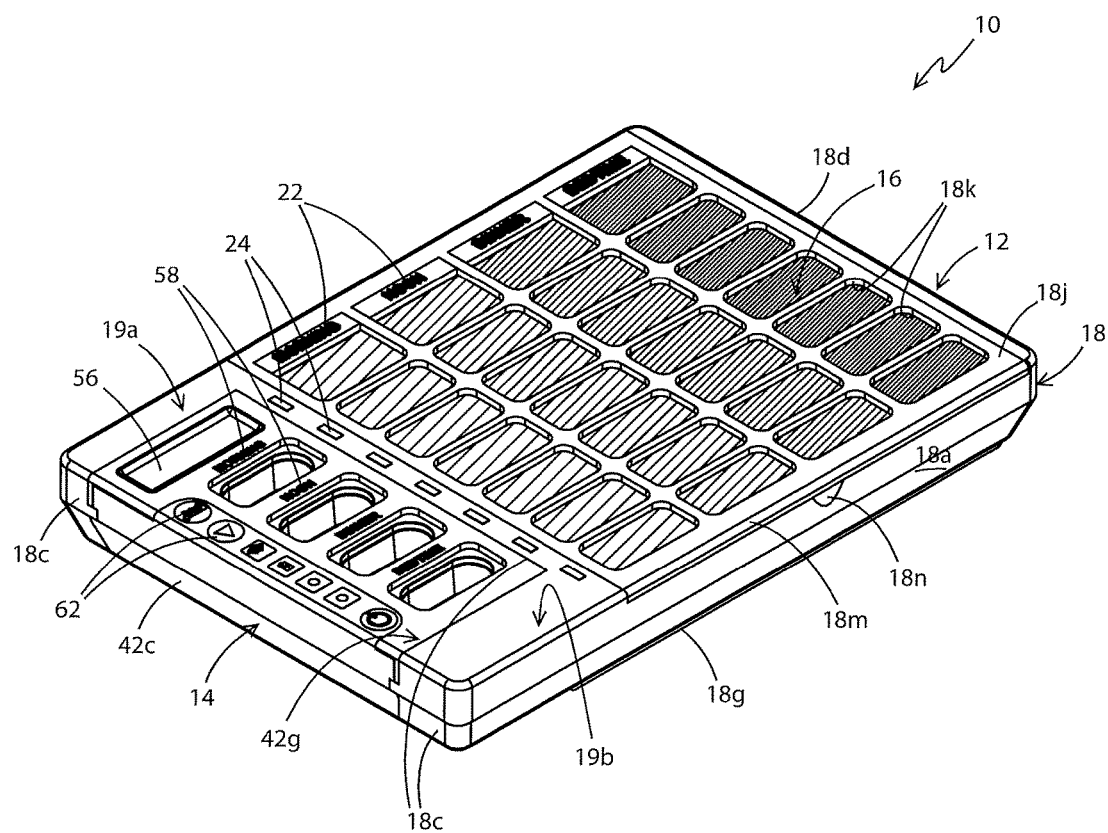
FIG. 1 is a top perspective view of an electronic pill box in accordance with an aspect of the present invention showing a base module and a day module engaged with each other and with the covers of the modules in a closed position.
Figure 2:
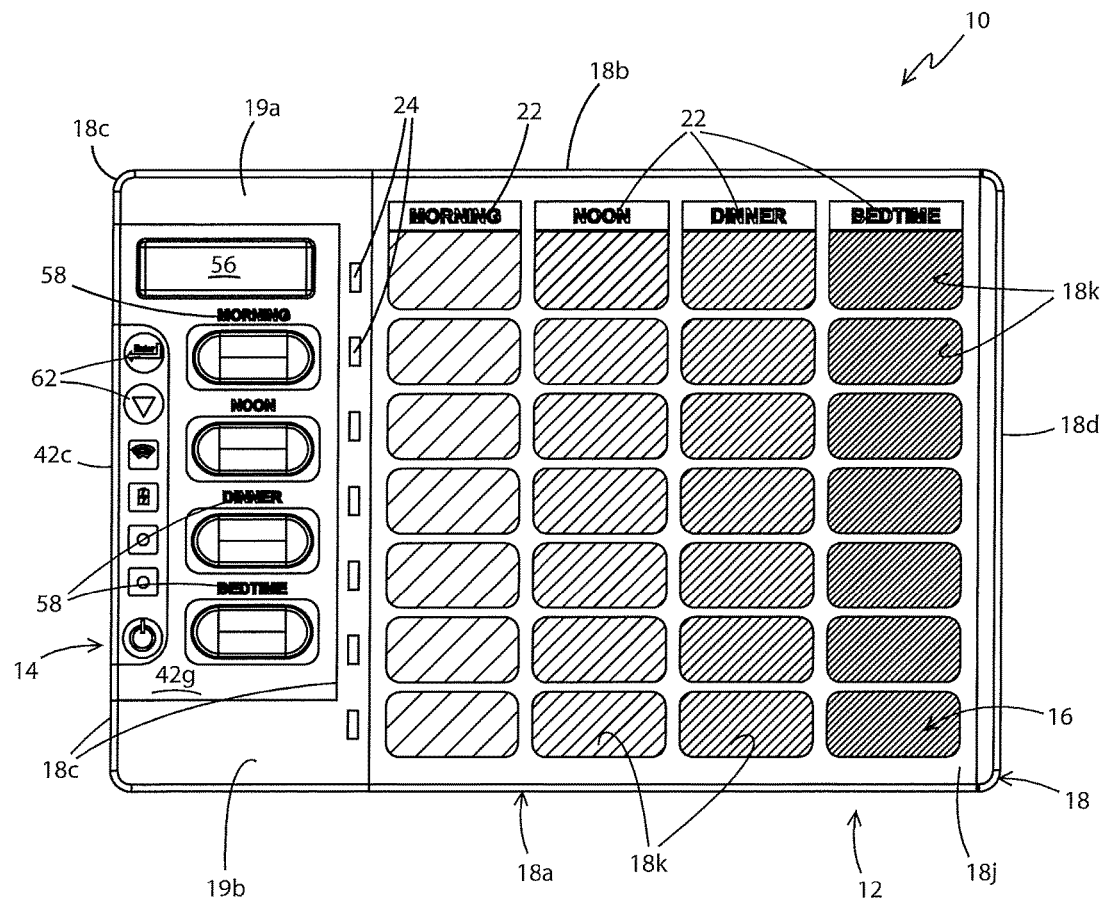
FIG. 2 is a top plan view of the pill box of FIG. 1.
Figure 3:
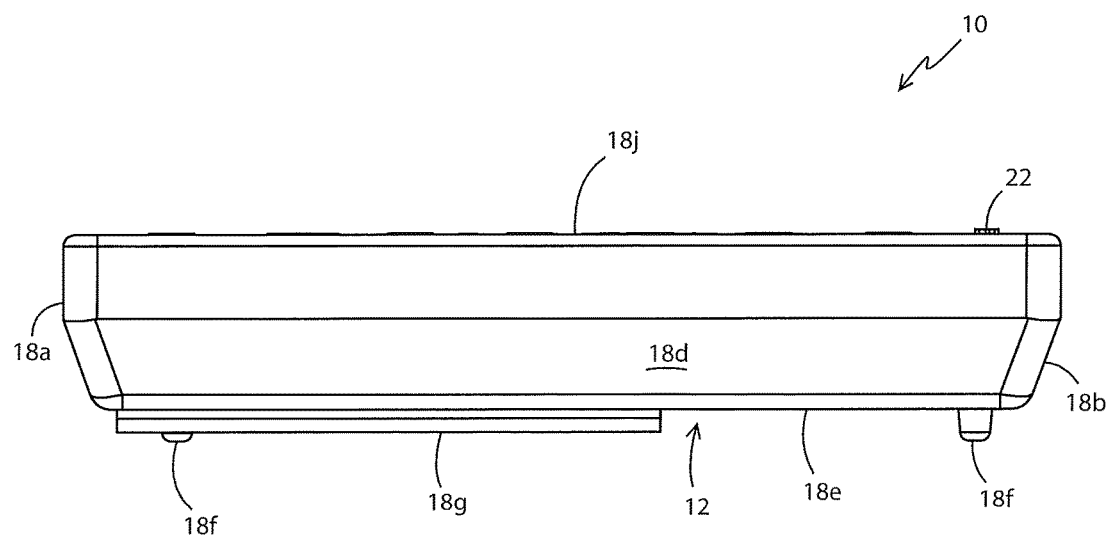
FIG. 3 is right side elevation view of the pill box.
Figure 4:
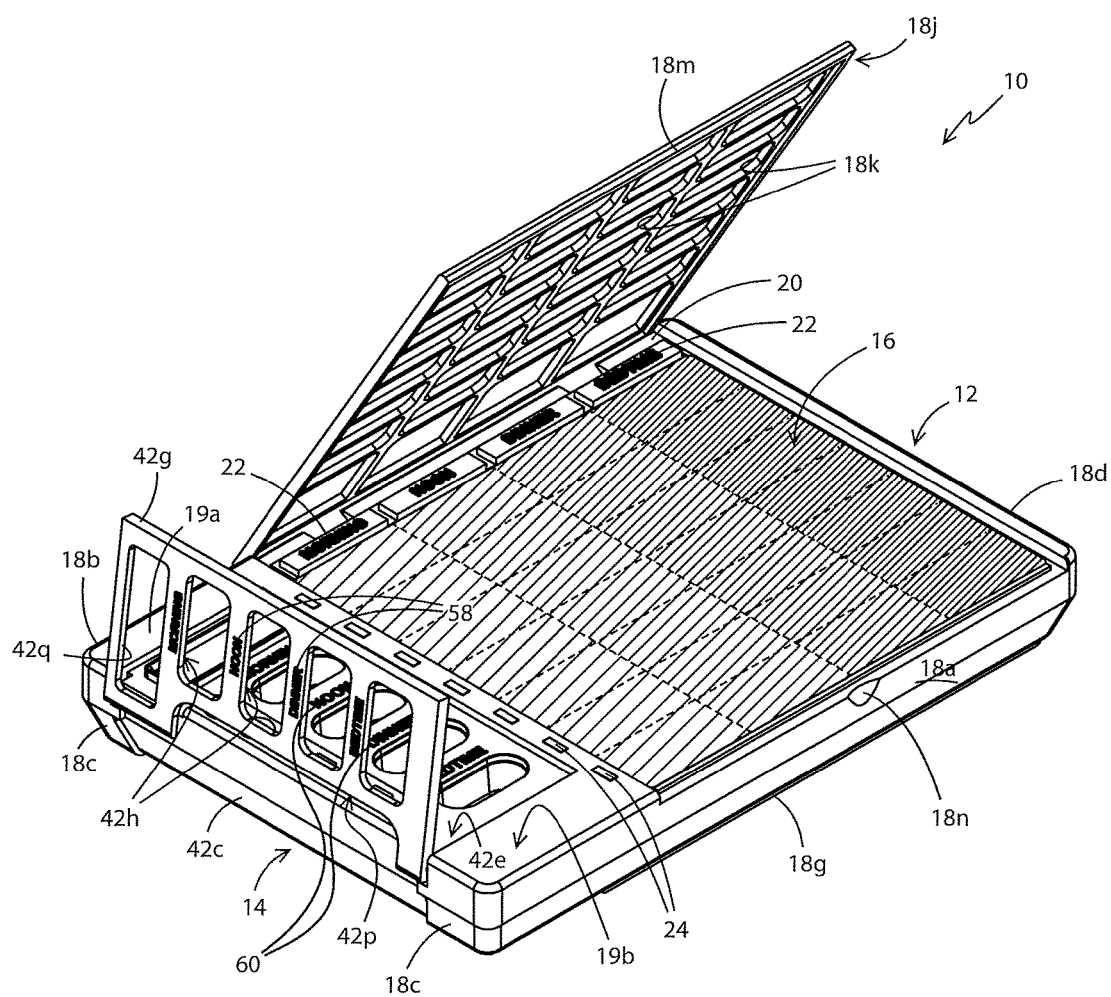
FIG. 4 is a top perspective view of the electronic pill box with the covers to the base module and day module moved to an open position and showing a blister pack loaded in the base module.
Figure 5:
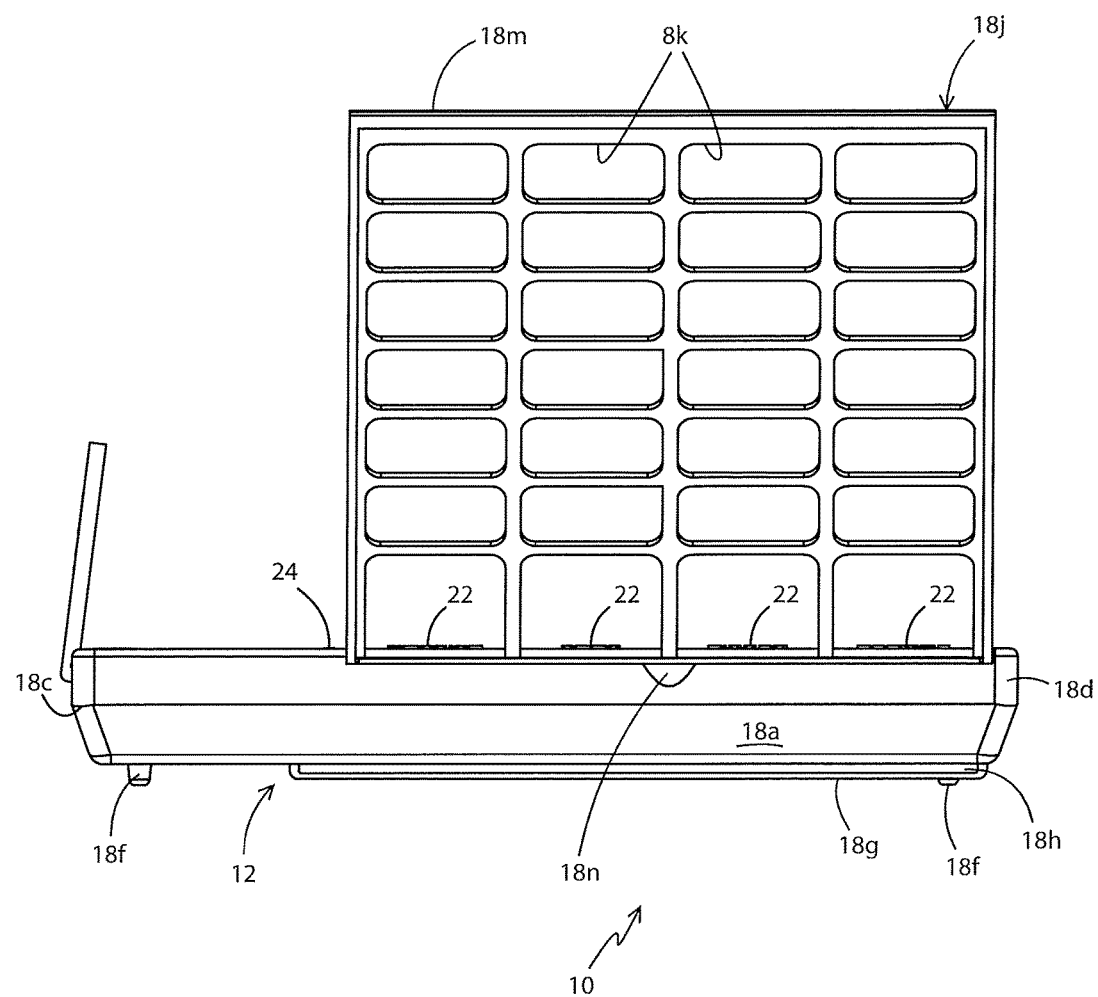
FIG. 5 is a front elevation view of the pill box as shown in FIG. 4.
Figure 6:
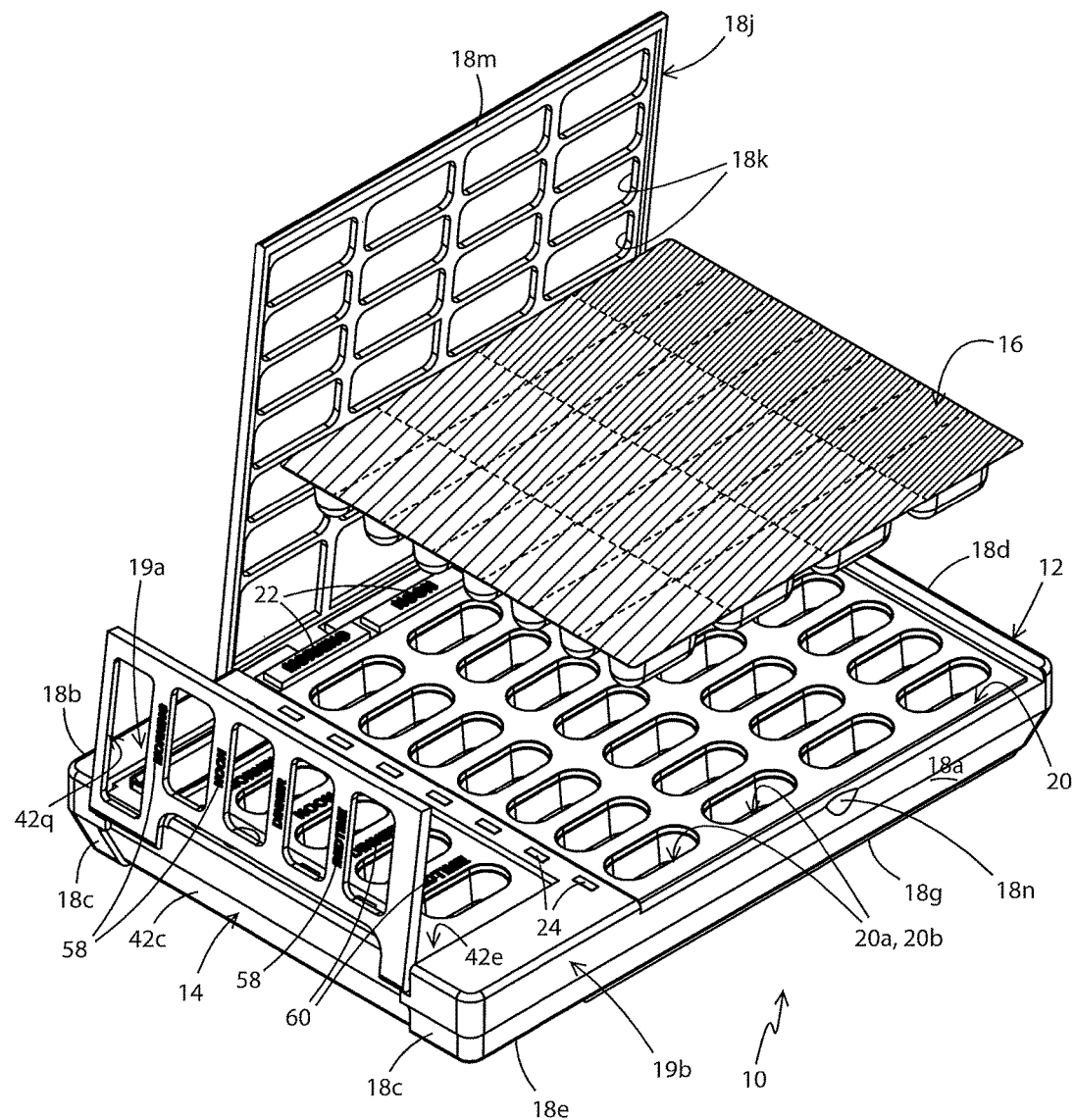
FIG. 6 is a top perspective view of the electronic pill box with the base module and day module covers in an open position and showing the blister pack exploded outwardly from the base module of the pill box.

Continuing to refer to FIGS. 1-10, housing 18 also comprises a cover 18j that is pivotally engaged with rear wall 18b and is movable between a closed position (FIG. 1) and an open position (FIG. 4). (It will be understood that cover 18j may, alternatively, be engaged with any other of the front wall 18a, first side wall 18c, second side wall 18d or even part of a top wall that is located opposite bottom wall 18e). Cover 18j defines a plurality of apertures 18k therein that extend between an interior surface and an exterior surface thereof. Cover 18j may define any desired number of apertures 18k therein. The cover 18j illustrated in the attached figures defines a total of twenty-eight apertures 18k arranged therein to correspond generally to the number of days in four weeks of a month. Base module 12 is therefore usable for the weekly or monthly dispensing of medication. Apertures 18k may be arranged in a pattern of seven rows and four columns. The seven rows may be used to represent the days of the week. The four columns may be used to represent the most typical times of day that medication must be taken, i.e., first thing in the morning, at noon, at dinner time and at bedtime. It will be understood that other column and row arrangements may be utilized in cover 18j instead of the one illustrated herein. Furthermore, the illustrated pattern of apertures 18k is a grid pattern but any other desired pattern may be utilized instead such as a series of concentric rings, spokes of a wheel, or isolated groupings spaced a distance from each other. Whatever pattern of apertures 18k utilized in cover 18j, each aperture 18k is positioned and shaped to align with one of a plurality of dosettes provided in blister pack 16, as will be hereinafter described. The pattern of the dosettes provided on blister pack 16 is thus arranged to be complementary to the pattern of apertures 18k on cover 18j. Each aperture 18k permits access to a peelable portion of the film or paper that is applied across an uppermost region of the associated dosette in blister pack 16. The apertures 18k are of a sufficient size to permit a user to peel back the peelable portion of the film or paper and gain access to the interior of any particular dosette.

Cover 18j may include a latching member 18m provided along a front edge thereof or along whichever edge of the cover 18j is located opposite the wall that includes hinges or a living hinge which permits rotation of cover 18j. Latching member 18m may be generally L-shaped when viewed from the side (see FIG. 11) and may be shaped to overlap an uppermost region of front wall 18a. Latching member 18m may engage and latch cover 18j to front wall 18a when cover 18j is moved to the closed position. Front wall 18a may also define a depression 18n therein. The user may insert a fingertip into depression 18n in order to engage latching member 18m and rotate cover 18j into the open position.

Front wall 18a, rear wall 18b, first side wall 18c, second side wall 18d and bottom wall 18e bound and define a cavity 18p (FIG. 11) in base module 12. Base module 12 may also include a top wall 20 (FIGS. 6, 11, & 13) that extends partially or entirely between front and rear walls 18a, 18b and between first and second side walls 18c, 18d. Base module 12 defines a first group of receptacles that receive dosettes 17 from blister pack 16. Day module 14 defines a second group of receptacles that receive individual dosettes 17 when they have been detached from the blister pack 16.

Figure 13:
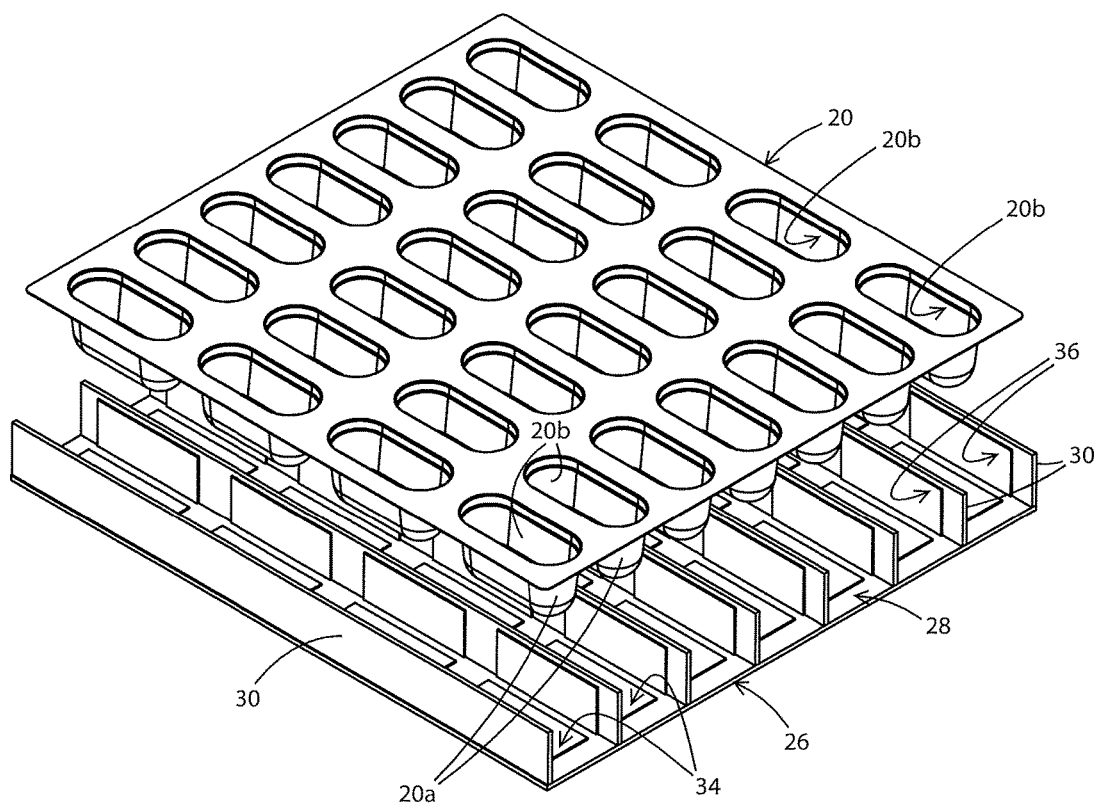
FIG. 13 is an exploded top perspective view of the base module PCB and the blister pack shown alone.

As shown in FIG. 13, top wall 20 may form part of an insert that is placed within housing 12 to close off access to cavity 18p. Top wall 20 may be oriented so as to be substantially parallel to bottom wall 18b of housing 18. Top wall 20 may define a plurality of receptacles 20a therein (the first group of receptacles) that extend for a distance downwardly from top wall 20 and into cavity 18p. Receptacles 20a may be of any desired shape and size. As illustrated in the attached figures, each receptacle 20a may be generally U-shaped in longitudinal and lateral cross-section and may bound and define a compartment 20b therein. Compartment 20b is accessible through an opening in top wall 20. The number and placement of receptacles 20a and the associated compartments 20b is generally complementary to the placement of apertures 18k in cover 18j when cover 18j is in the closed position. Each receptacle 20a is located so as to be vertically below one of the apertures 18k in cover 18j when cover 18j is in the closed position. Receptacles 20a may be organized in a pattern of rows and columns that is complementary to the pattern of apertures 18k in cover 18j and any desired number of rows and columns of receptacles 20a and apertures 18k may be provided. The attached figures show a housing 18 in which the top wall 20 defines seven rows of receptacles 20a and four columns of receptacles 20a for a total of twenty-eight receptacles in base module 12. Cover 18j similarly includes seven rows of apertures 18k and four columns of apertures 18k. Each aligned row of apertures 18k and receptacles 20a may represent one of the days of the week and each aligned column of apertures 18k and receptacles 20a may represent a time of day. A plurality of time indicators 22 may be provided to identify to the user the day of the week and/or the time of day. Time indicators 22 may be provided on an outer surface of cover 18j or on part of the exterior surface of top wall 20 and extending through an associated aperture 18k of cover 18j. This latter instance is illustrated in FIG. 4. The time indicators 22 may alternatively or additionally be provided on an exterior surface of blister pack 16 that is engaged with housing 18. Wherever and however these time indicators 22 are provided on housing 18, time indicators 22 may include words such as "Morning", "Noon", "Dinner" and "Bedtime". Other indicia may be used instead of these words. For instance specific times of day, such as "6 am", "12 pm" "6 pm" etc. may be used as time indicators 22 or the indicators 22 may include a combination of words and numbers. Time indicators 22 may be used to visually remind a patient when to take a particular dose of medication.

Light pipes 24 may be provided adjacent each row (or column) of receptacles 20a. Light pipes 24 may be positioned and configured to illuminate specific dosettes or rows of dosettes on blister pack 16 at pre-determined times. Light pipes 24 are operatively engaged with a microcontroller 38 (FIG. 14) that includes programming to illuminate specific light pipes at specific times. If desired, tabs with words or other indicators may be provided superimposed over light pipes 24 so that the words or other indicators over light pipes 24 may be illuminated to draw the patient's attention. Alternatively, the words or other indicators may be provided adjacent light pipes 24. Still further, instead of a light pipes 24 being provided at one end of each row on housing 18, illumination sources may be provided beneath top wall 20 or within compartment 20b of each receptacle 20a or beneath each compartment 20b. Any suitable and desired configuration of day and time indicators and lighting systems for the receptacles 20a may be utilized to draw the patient's attention to particular dosettes on blister pack 16 when engaged in housing 18. This arrangement will better enable the patient to know when to take medication from any particular dosette.

An electronic reminder system for alerting the patient has been described in copending U.S. patent application Ser. No.

14/858,041 filed Sep. 19, 2015 and in copending U.S. patent application Ser. No. 13/965,966 filed Aug. 13, 2013 by the inventors named herein; and the disclosures of both of these applications are incorporated herein by reference. Because the electronic reminder system has been described in detail in these two applications, the system will not be further described herein but it should be understood that the electronic pill box 10 herein functions in substantially the same manner as a reminder and compliance system for the patient. Pill box 10 includes a first electronic reminder system in base module 12 and a second electronic reminder system in day module 14. The first and second electronic reminder systems are operatively engaged with each other when day module 14 is engaged with base module 12 and operate as a single system. When day module 14 is disengaged from base module 12, the first and second electronic reminder systems operate independently but on the same schedule for the patient. The reminder systems are comprised of the electronic components utilized in each of the base and day modules 12, 14 and in the programming that operates the same.

Blister pack 16 is configured to be selectively engaged with housing 18. Blister pack 16 is configured to be complementary to top wall 20 and to be seated thereon. As shown in FIG. 7, blister pack 16 comprises a horizontal wall 16a that is substantially similar in shape and size to top wall 20 and wall 16a defines a plurality of receptacles 16b therein (the second group of receptacles referenced earlier herein) that extend downwardly from a lower surface of wall 16a. Receptacles 16b are complementary in shape, size, number, location and pattern to compartments 20b of top wall 20. Receptacles 16b are configured to nest within compartments 20b when blister pack 16 is seated on top wall 20. Each receptacle 16b bounds and defines a compartment 16c that is accessible through an opening in wall 16a.

A film 16d covers the wall 16a and closes off access to the openings to all the compartments 16c. This film 16d may comprise a plastic film, a metal film, a paper film or any other film that can close off access to the various compartments 16c. Medication "P" (FIG. 11) is placed within the compartment 16c of each receptacle 16b of blister pack 16. Film 16d is then applied over wall 16a to seal the doses of medication "P" within the various receptacles 16b. Blister pack 16 may be pre-loaded with a number of doses of medication "P" for a particular patient.

Blister pack 16 and film 16d of blister pack 16 may include a plurality of lines of weakness 16e, 16f that divide blister pack 16 and the film 16d thereon into smaller sections. Each individual compartment 16c with its associated receptacle 16c for receiving a dose of medication "P" and which is covered by a section of film 16d comprises one of the dosettes 17 of blister pack 16. The individual dosettes 17 are initially connected together in a side-by-side arrangement and remain so when blister pack is engaged with base module 12. Individual dosettes 17 may be separated from blister pack for engagement with day module 14. Lines of weakness 16e, 16f allow individual dosettes 17 to be separated from the rest of blister pack 16. Lines of weakness 16e in film allow the user to depress or lift a portion of film 16d from an individual receptacle 16b so that the dose of medication "P" retained within that receptacle 16b may be accessed by the patient. Film 16d may be selectively peeled off a single compartment/receptacle 16b, 16c while the associated dosette 17 remains connected to blister pack 16. When a dosette 17 has been detached from blister pack 16, the portion of the film 16d covering the same may be peeled back to access the medication therein.

FIG. 7 shows each column of dosettes 17 in blister pack 16 shaded differently. This different shading is utilized to show that each column of dosettes is color-coded, i.e., the dosettes may each have a different color film 16d covering the receptacles 16b in that particular column. For example, the film 16d on the first column of dosettes 17, represented by the letter "A", may be of a first color; the film 16d on the second column of dosettes represented by the letter "B' may be of a second color; the film 16d on the third column of dosettes represented by the letter "C" may be of a third color; and the film on the fourth column of dosettes represented by the letter "D" may be of a fourth color. The first color "A" represents a first time of day that the patient needs to take a dose of medicine, the second color "B" represents a different second time of day that the patient needs to take a does of medicine. The third color "C" represents a third time of day and the fourth color "D" represents a fourth time of day at which the patient needs to take their medicine. These different colors "A" through "D" are used to provide the patient with a quick and easy visual indicator of the time of day that a particular dosette 17 should be opened. For example, dosettes "C" may include medication "P" that is only to be taken at dinner time and dosettes "A" may include medication "P" that is only be taken at breakfast. This color coding may also be of assistance to patients when loading day module 14 as the color needs to match a particular compartment in the day module 14. The patient is able to ensure they are placing the appropriate medication in a particular dosette 17 by comparing the color of the film on that dosette with the color film of the part of the blister pack 16 that is in the column representing the time of day the medication is meant to be taken. So, for example, if the blister pack's morning column includes a blue film, then the patient will know to place a blue-colored dosette 17 in the "morning" compartment of day module 14. The color of film 16d is also utilized by pill box 10 to check the patient has loaded the correct medication in the correct position in day module. This will be later described herein.

When blister pack 16 is to be engaged with housing 18, cover 18j of housing 18 is moved to the open position and blister pack 16 is seated on top of wall 20. The lower surface of wall 16a is placed adjacent the upper surface of top wall 20 and receptacles 16b are positioned to be s received in one of the compartments 20b. Cover 18j is then moved to the closed position, trapping blister pack 16 between top wall 20 and the interior of cover 18j. Cover 18j is latched into place by engaging latching mechanism 18m. When blister pack 16 is trapped in this manner, apertures 18k in cover 18j may align generally with the lines of weakness 16e in film 16d. It is therefore possible for the user to peel back a section of film 16d covering a particular dosette 17 by inserting fingertips through the associated aligned aperture 18k.

Figure 12:
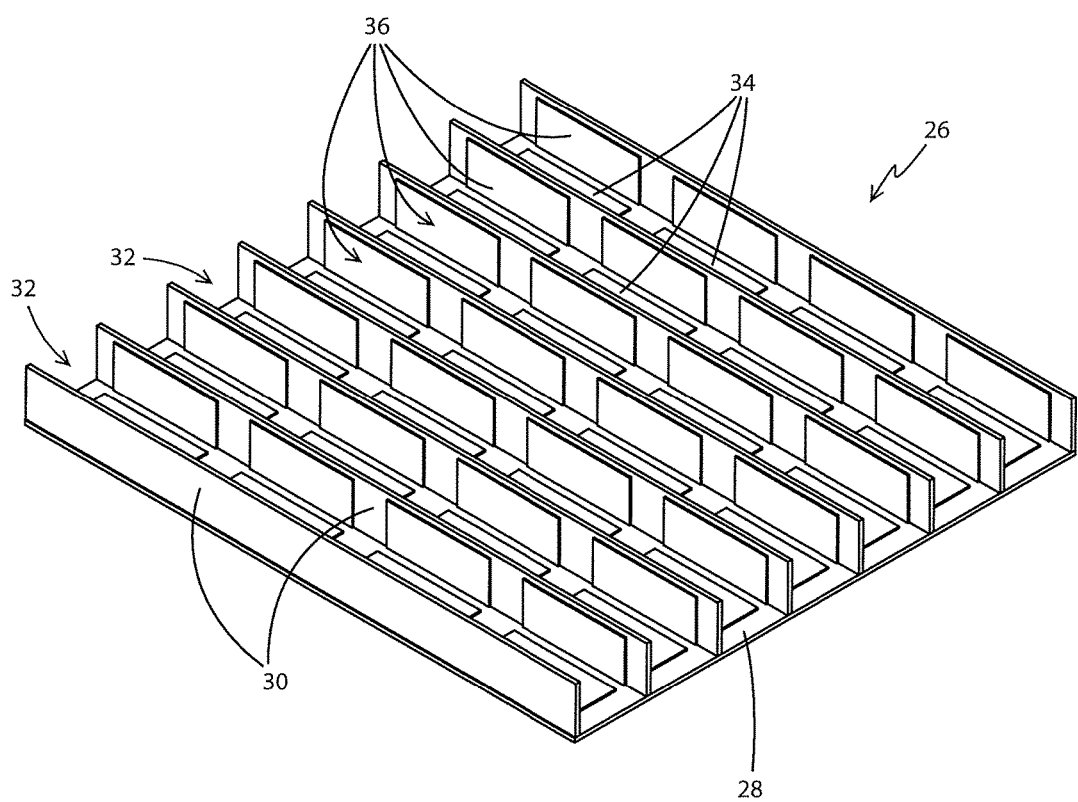
FIG. 12 is a top perspective view of the printed circuit board PCB of the base module illustrated on its own.
Figure 14:
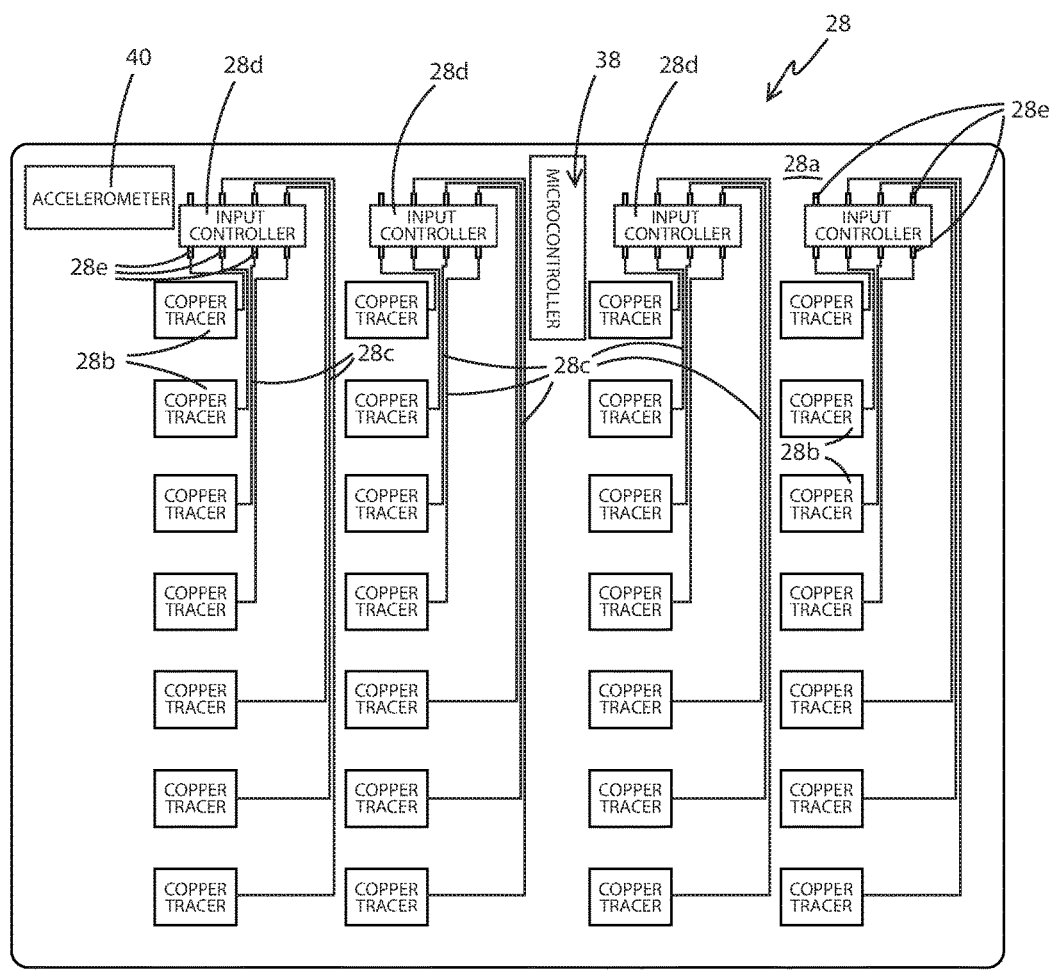
FIG. 14 is a top plan view of the PCB for the base module with the upstanding side PCBs and the insulating covering removed to reveal some of the electronic components of the PCB.

Referring to FIGS. 12-14, housing 18 also includes a circuit board assembly 26 that comprises a main printed circuit board (hereafter referred to as main PCB 28) and a plurality of vertically upstanding side printed circuit boards (hereafter referred to as side PCBs 30). Side PCBs 30 are oriented at right angles to main PCB 28 and are arranged in a plurality of generally parallel, spaced-apart rows. A gap 32 is defined between each pair of adjacent side PCBs 30. Each gap 32 is of a sufficient size so as to ensure that a row of receptacles 20a will be able to fit between adjacent side PCBs 30. A plurality of first capacitance sensors are provided in the form of bottom sensors 34 located on the upper surface of main PCB 28 within each gap 32. Bottom sensors 34 may be located at spaced intervals from each other. Each bottom sensor 34 is located on main PCB 28 in a position that will cause it to be positioned beneath a bottom wall of one of the receptacles 20a of top wall 20. Bottom sensors 34 are spaced a distance away from a bottom wall of the associated receptacle 20a. A plurality of second capacitance sensors are provided in the form of side sensors 36 that are located at spaced apart intervals along each side PCB 30. Each side sensor 36 is positioned to align with one of the side walls of one of the plurality of receptacles 20a of top wall 20. Side sensors 36 are spaced a distance from the side walls. FIG. 11 shows that a side sensor 36 may be located adjacent each of the two longitudinal side walls of each receptacle 20a.

Main PCB 28 is illustrated in FIG. 14 as including a substrate 28a, a plurality of copper tracers 28b, tracer connections 28c, input controllers 28d, and input pads 28e. There may be about 8 input pads 28e per input controller 28d. Main PCB 28 may also include a microcontroller 38 and an accelerometer 40. Microcontroller 38 may be provided with programming to control base module 12 and day module 14 when engaged with base module 12. Microcontroller's programming causes pill box 10 to operate as an electronic reminder system for taking medication in a timely fashion. The PCB tracers 38b shown in FIG. 14 are used as the capacitance sensors, i.e., as bottom sensors 34 and side sensors 36. The capacitance sensors 34, 36 are thus relatively simple copper areas on the main PCB 28 and size PCBs 30 and are connected to the sensor inputs 28e of the sensor input controllers 28d (hereafter sensor IC 28d). Each sensor IC 28d may have eight pad inputs 28d and because there are twenty-eight days of receptacles 20a, 16b provided in base module 12, twenty-eight sensor pads inputs 28d are utilized. Four sensor ICs 28d are used to cover the entire pads array. The copper area of each sensor pad 28d/34/36 may be of any suitable size and shape. The capacitive sensor PADs 28d may be covered by an isolating overlay material. As capacitance change is able to be detected through air, medication "P" located within the compartments 16c of receptacles 16b of blister pack 16 is able to be detected. (The bottoms of receptacles 16b may be located around 1 mm-2 mm above the sensor pads 34. Unlike other variations of capacitance sensing, no direct connection is needed in housing 18. In other words, neither the medication "P" nor the blister pack 16 needs to touch the capacitance sensors 34 in order for detection of the medication "P" or lack thereof to occur. Side sensors 36 aid in providing accurate detection of medication "P" within any particular compartment 16c.

The bottom side and surrounding area of the PCB sensor pads 34, 36 is covered by grounding copper fills. Capacitance sensors IC 28d measure the change of charge and covert that information into digital values. It is also possible to use analog output with proper filtering. The larger the charge on the sensors 34, 36, the larger the absolute value will be. The charge to value conversion is done by an Analog Sensor Interface (ASI). The digital values are further processed by the sensor ICs 28d and converted into high level information for microcontroller 38. The information between sensor ICs 28d and microcontroller 38 is passed through a 12C/spi or parallel interface with an additional interrupt signal indicating that one sensor IC 28d has new information. The four sensor ICs are used and interrupts are multiplexed and connected to microcontroller 38. On getting interrupt signals, microcontroller 38 pulls the sensor registers one by one to see which pad 34 or 36 has capacitance change detected.

The ASI consists of a multiplexer selecting the sensor, analog switches, a reference voltage, a high-resolution ADC converter and an offset compensation DAC (Digital to Analog Converter). To get the digital value representing the charge on a specific sensor 34, 36, the ASI will execute several steps. To get the digital value representing the charge on a specific sensor pad 34, 36, the ASI will execute the several steps. A voltage will be induced on the sensor 34, 36, developing a charge relative to the absolute capacitance of the sensor. The charge on the sensor pad 34, 36 will then be accumulated multiple times on the internal integration capacitor (Cint). This results in an increasing voltage on Cint proportional to the capacitance on pad 34, 36. At this stage, the offset compensation DAC is enabled. The compensation DAC generates a voltage proportional to an estimation of the external parasitic capacitance (the capacitance of the environment and system without the calibration.) The difference between the DAC output and the charge on Cint is the desired signal. In the ideal case, the difference in charge will be converted to a zero digital value if no medication "P" is present in a particular compartment 16c. The digital value becomes high in the instance where medication "P" or a user's fingertip is present in any compartment 16c.

The raw data is processed through a programmable low pass filter to create useful data (data with fast environmental noise suppressed). The useful data is processed through a second programmable low pass filter (with a longer time constant) to create average data. The average data tracks along with the slow environmental changes and is subtracted from the useful data to create the diff data. The diff data represents any fast capacitance changes such as medication "P" being removed from a compartment 16c or a medication proximity event.

The parasitic capacitance at the sensor IC pins is defined as the intrinsic capacitance of the integrated circuit, the PCB traces, ground coupling and the sensor planes. This parasitic capacitance is relatively large (tens of pF) and will also vary slowly over time due to environmental changes. The proximity of medication "P" is in the order of one pF and its effect typically occurs much faster than the environmental changes. The ASI has the difficult task of detecting small, fast changing capacitance that is riding on a large, slow varying capacitance. This may require a very precise, high resolution ADC and complicated, power consuming, digital processing. The Sensor IC may feature a 16 bit DAC that compensates for the large, slow varying capacitance already in front of the ADC. In other words, the ADC converts only the desired small signal. In the ideal world, the ADC will put out a zero digital value even if the external capacitance is as high as 34 pF.

At each power-up of the sensor IC 28d, the compensation values are estimated by the digital processing algorithms. The algorithm will adjust the compensation values such that a near-zero value will be generated by the ADC. Once the correct compensation values are found these will be stored and used to compensate each pad pin. If the sensor IC 28d is shut down, the compensation values will be lost. At a next power-up the procedure starts all over again. This assures that the sensing will operate under any condition. If temperature changes then the external capacitance may be influenced. The ADC digital values will then drift slowly around zero values basically because of the mismatch of the compensation circuitry and the external capacitance. In case the average value of the digital values becomes higher than the positive calibration threshold (configured by the microcontroller 38) or lower than the negative threshold (configured by the microcontroller 38), then the sensor IC 28d will initiate a compensation procedure by using the 12C interface on Reset or power-up.

Capacitance sensor IC detects the proximity object and sends the capacitance value after filtering to the microcontroller 38, either by interrupt or by updating internal register (polling mode). The microcontroller 38 reads sensor IC registers and makes a judgement based on the value that medication "P" is present or is not present in any particular compartment 16c.

Single pill capacitance, for example, is used as a threshold more than one pill may be identified based on the capacitance value read from the register.

As a pill's proximity is detected through capacitance, moving the box vertically may shift pills "P" in the blister pack 16 and can give false readings. In order to avoid this, the accelerometer 40 is provided on main PCB 28. Accelerometer 40 is used to detect when housing 18 is in the correct orientation for valid readings. When the housing's orientation is incorrect, for example, if the housing is vertical or being shaken or moved, the sensor ICs interrupt is disabled and/or values are discarded. The accelerometer 40 correct position is used to accept the proximity capacitance values.

Referring mainly to FIGS. 15-21, day module 14 comprises a separate unit that may be interlockingly engaged with base module 12. Day module 14 is selectively disengaged from base module 12 when the patient desires to carry a smaller electronic pill box in a purse or pocket, for example. In these instances day module 14 is readily detached from base module 12 by pulling day module 14 outwardly away from base module 12 in the direction of arrow "P" (FIG. 8). (Day module 14 may be reengaged with base module 12 by aligning various locking components on day module 14 with mating components on base module 12 and then pushing day module 14 in the opposite direction to arrow "P" until the various locking components interlockingly engage day module 14 and base module 12 to each other.)

Day module 14 is in essence a miniaturized version of base module 12 and may include substantially all of the components necessary to make day module 14 operate as a separate electronic reminder system for taking medication "P" at prescribed time intervals. Each of base module 12 and day module 14 may include a separate power source so that the modules may be independently operated. The power sources are operatively engaged with the respective electronic components in day module 14 or base module 12.

Figure 16:
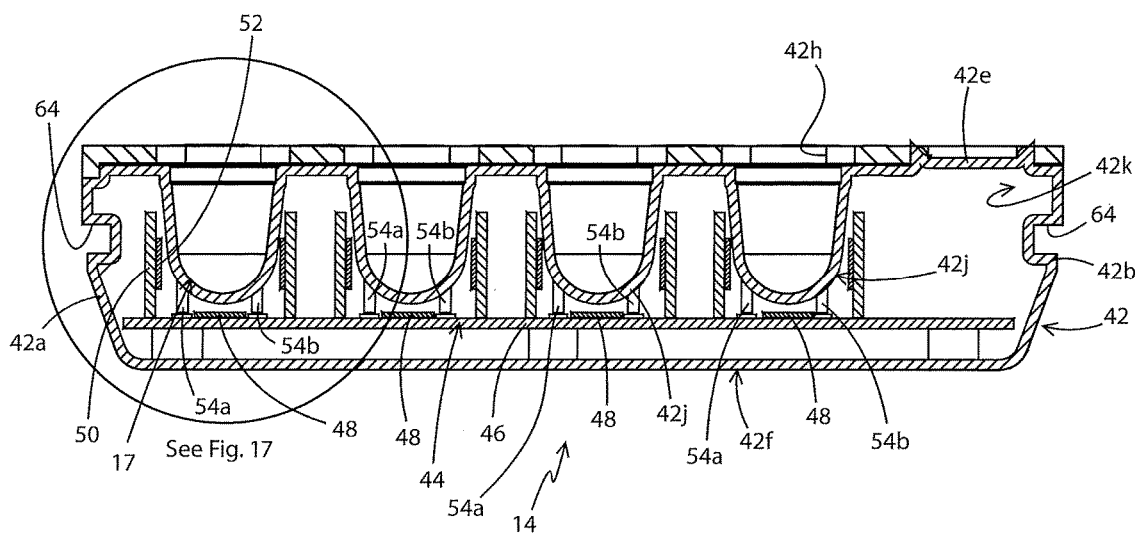
FIG. 16 is a cross-section of the day module taken along line 16-16 of FIG. 15.
Figure 17:
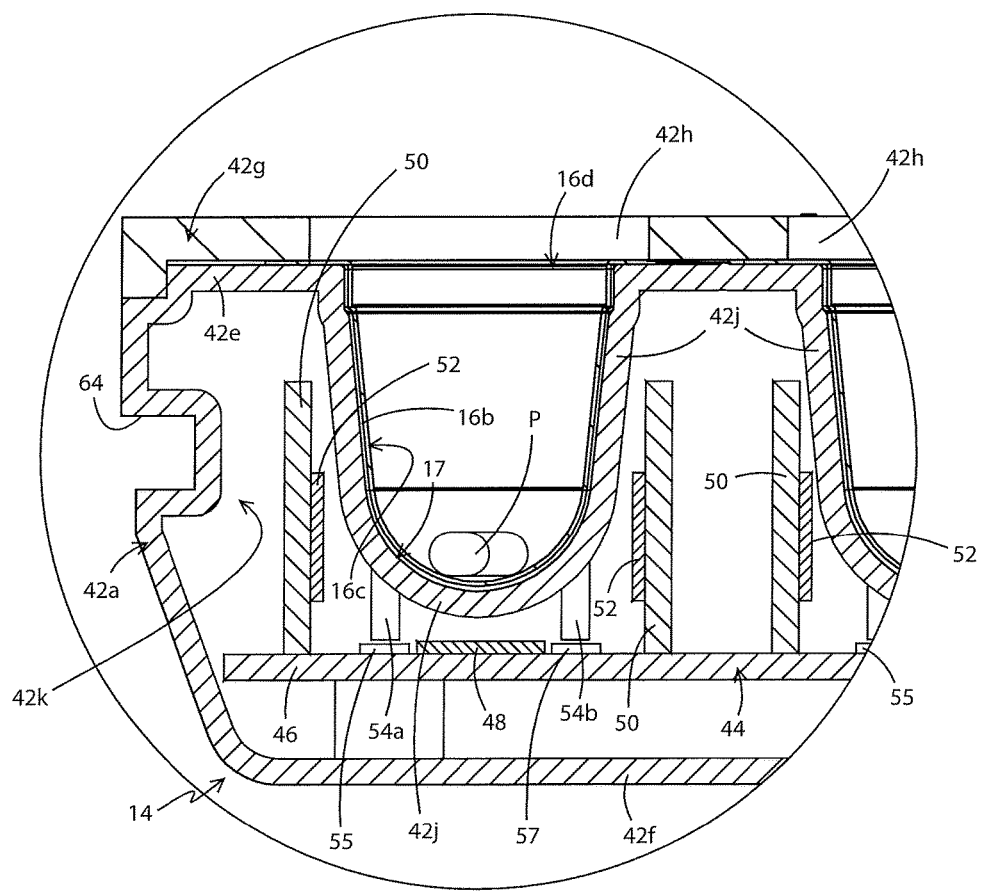
FIG. 17 is an enlargement of the highlighted region of FIG. 16.
Figure 18:
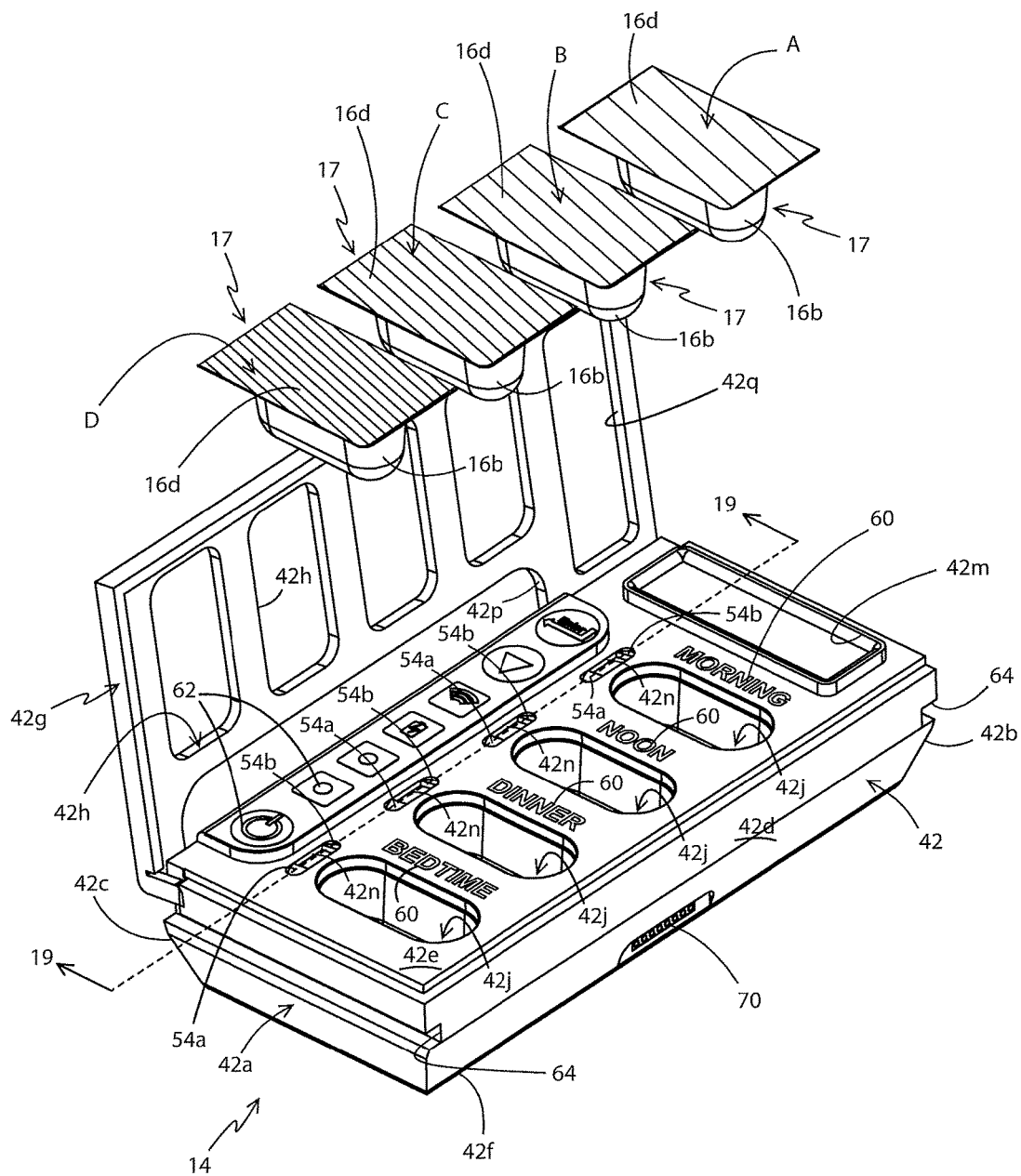
FIG. 18 is a right side perspective view of the day module shown on its own and in an open position and showing the four individual dosettes exploded outwardly therefrom.
Figure 19:
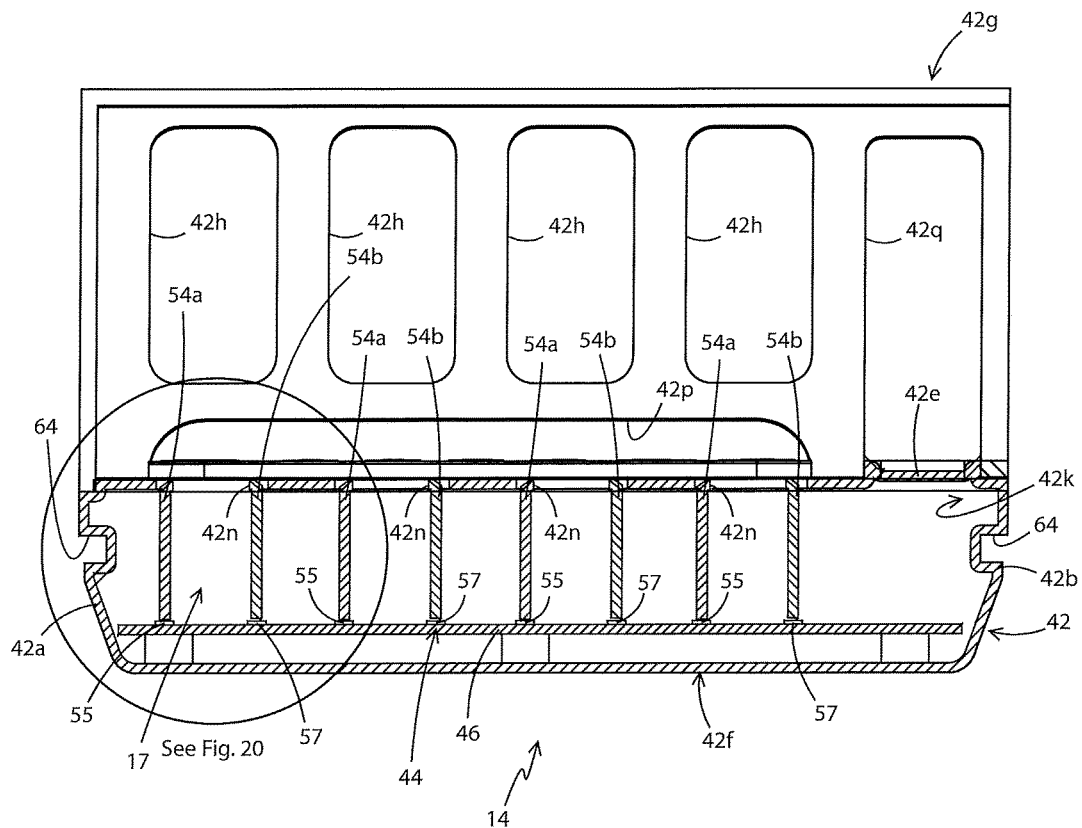
FIG. 19 is a cross-section of the day module taken along line 19-19 of FIG. 18.

Referring to FIGS. 1, 4, 9, and 15-21, day module 14 includes a housing 42 having a front wall 42a, a rear wall 42b, a first side wall 42c, a second side wall 42d, a top wall 42e (FIG. 4) and a bottom wall 42f (FIG. 9). A cover 42g is pivotally engaged with first side wall 42c and is movable between a closed position (FIG. 15) and an open position (FIG. 18). It will be understood that cover 42g may be engaged with any other of the front wall 42a, rear wall 42b, top wall 42e, or second side wall 42d instead of with first side wall 42c.

Figure 15:
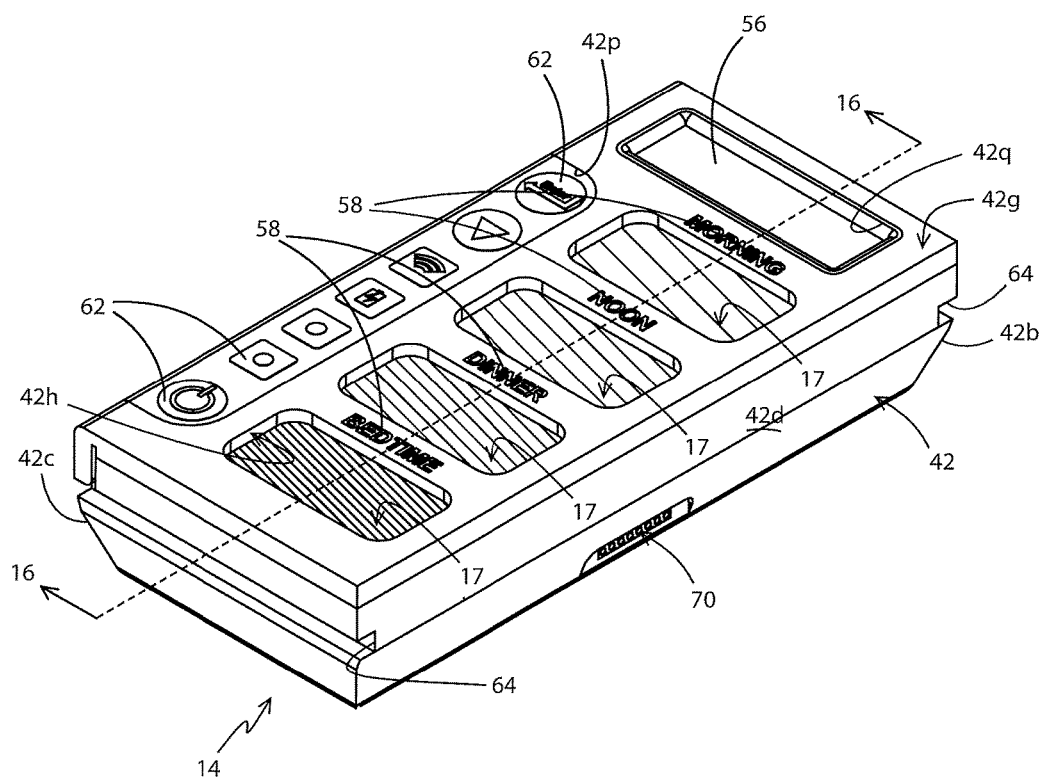
FIG. 15 is a right side perspective view of the day module shown on its own and in a closed position.

Cover 42g defines a plurality of apertures 42h (FIG. 4) therein that extend between an interior and exterior surface of cover 42g. A plurality of receptacles 42j is defined in top wall 42e of day module 14 and extends downwardly from a lower surface thereof and into a cavity 47k (FIG. 16) defined by front wall 42a, rear wall 42b, first and second side walls 42c, 42d and top and bottom walls 42e, 42f. Each receptacle 42j has a compartment that is substantially identical in shape and size to the receptacles 20b in wall 20 of base module 12 and is configured to receive the receptacle 16b of one of the individual dosettes 17 to be loaded into day module 14 therein. Each aperture 42h in cover 42g of day module 14 is positioned and shaped to align with one of the receptacle 42j in top wall 42e when cover 42g is moved to a closed position (FIG. 15).

Figure 21:
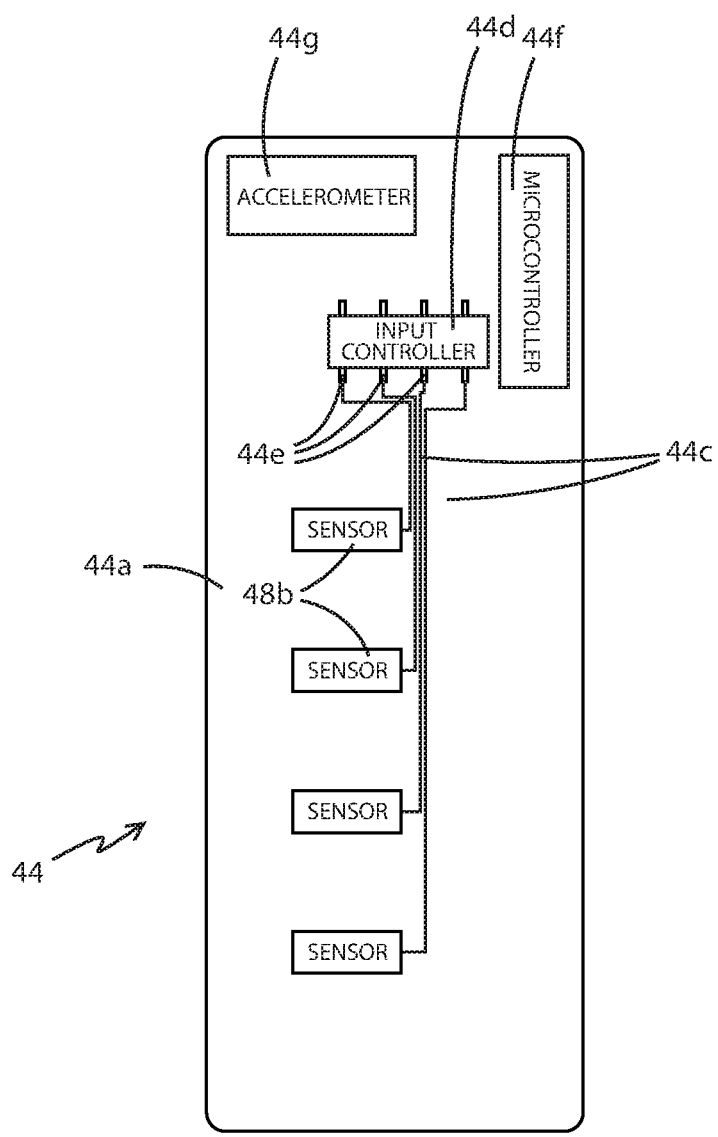
FIG. 21 is a top plan view of the PCB for the day module with the upstanding side PCBs and the insulating covering removed to reveal some of the electronic components of the PCB.

As illustrated in FIGS. 16, 17 and 21, a day module PCB 44 is provided within cavity 42k and this PCB 44 is similar in structure to PCB 26 in base module 12 except that PCB 44 is smaller in size. PCB 44 includes a main PCB 46 that is oriented generally parallel to top wall 42e. Main PCB 46 is provided with a plurality of first capacitance sensors in the form of the spaced-apart main sensors 48. Each sensor 48 is positioned a spaced-distance below a bottom wall of one of the receptacles 42j that extends downwardly into cavity 42k. Main PCB 44 also includes vertically oriented side PCBs 50 oriented at right angles to main PCB 46 and separated from each other by gaps. Each side PCB 50 includes a plurality of second capacitance sensors in the form of spaced-apart side sensors 52. Each side sensor 52 may be positioned spaced-apart from but adjacent to one of the side walls of one of the receptacle 42j extending into cavity 42k.

FIG. 21 shows the main PCB 44 of the day module 14 with the isolating overlay material removed therefrom. PCB 44 includes a substrate 44a, a plurality of copper tracers 44b, tracer connections 44c, input controllers 44d, and input pads 44e (around 4 input pads 44e per input controller 44d). PCB 44 may also include a microcontroller 44f and an accelerometer 44g. Microcontroller 44f may be provided with programming to control day module 14 and to operate the day module as a portable electronic reminder system for taking medication in a timely fashion. The PCB tracers 44b may be used as the capacitance sensors 48. The capacitance sensors 48 are thus relatively simple copper areas on the main PCB 46 and are connected to the sensor inputs 44e of the sensor input controllers 44d (hereafter sensor IC 44d). Each sensor IC 44d may have four pad inputs 44d because there are four receptacles 42j provided in day module 14. The copper area of each sensor pad 48, 52 may be of any suitable size and shape. The capacitive sensor PADs may be covered by an isolating overlay material.

It should be noted that the electronic reminder systems in base module 12 and day module 14 and their associated microcontrollers 38 and 44f include programming that will result in both modules following the reminder schedule for a patient. That way, when day module 14 is detached from base module 12, the reminders at the necessary times of day will be issued to the patient. There is no need to enter any information to tell the day module 14 which reminder schedule to follow. When base module 12 and day module 14 are engaged, the microcontrollers 38, 44f will be synced so that information is updated in real time.

Day module 14 includes a light sensor assembly to help ensure that the dosettes 17 placed therein are loaded into the correct positions within module 14. This system ensures that the patient will take the correct medication at the correct time of day. As part of the light sensor assembly, top wall 42e of day module 14 may define four openings 42n therein, where each opening 42n is located adjacent one end of one of the receptacles 42j. Openings 42n are defined between an interior and exterior surface of top wall 42e. Openings 42n may be located between controls 62 and receptacles 42j. Light pipes 54 of the light sensor assembly extend vertically upwardly from proximate main PCB 46 and terminate proximate openings 42n. Light pipes 54 may be substantially identical to light pipes 24. Preferably, however, light pipes 54 may be arranged in pairs 54a, 54b, with each pair being arranged to terminate proximate one of the openings 42n in top wall 42e. Light pipes 54a, 54b extends inwardly and downwardly from opening 42n into cavity 42k. The light sensor assembly also includes a light source and light sensor that are operatively engaged with microcontroller 44f. A suitable light source, such as LED 55 is provided on main PCB 46 in a position that places each LED 55 beneath a bottom end of one of the light pipes 54a and therefore remote from opening 42n. A color sensor or light sensor 57 may be located on main PCB 46 in such a position that sensor 57 is beneath a bottom end of one of the light pipes 54b and therefore remote from opening 42n. Light pipes 54, LEDs 55 and sensors 57 are operatively engaged with microcontroller 44f and microcontroller's programming is used to control light pipes 54, LEDs 55 and sensors 57 and to gather data therefrom.

Figure 20:
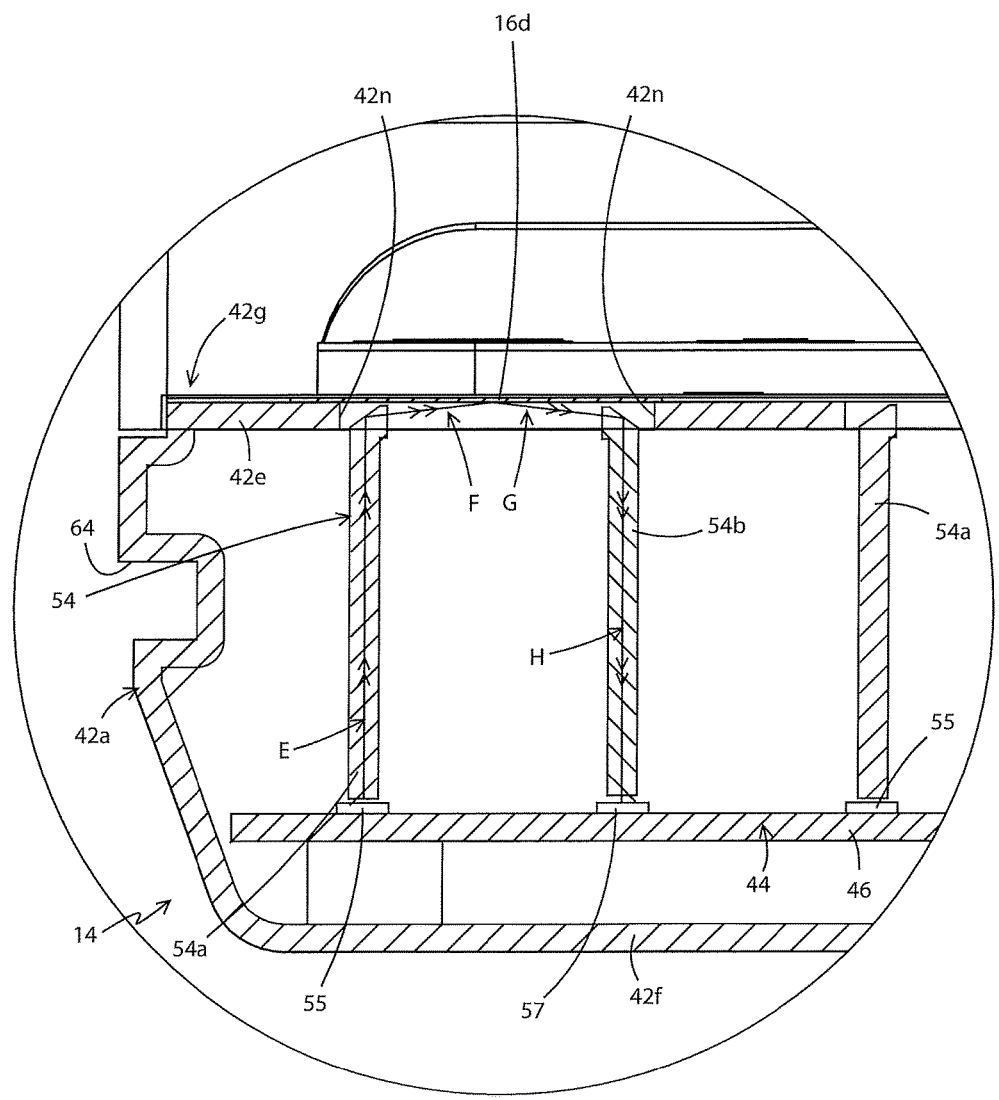
FIG. 20 is an enlargement of the highlighted region of FIG. 19.

As best seen in FIG. 20, light is emitted from LED 55 and into the bottom end of light pipe 54a in the direction of arrow "E". Light travels upwardly along light pipe 54a in the direction of arrow "E"; is reflected in the direction "F" off an angled upper surface of light pipe 54a and onto an underside of the colored film or paper 16d on one end of the dosette 17 located in the associated receptacle 42j. The light is subsequently reflected off film or paper 16d in the direction of arrow "G" and into an angled upper surface of light pipe 54b. The light is reflected off the angled upper surface and travels down the interior of light pipe 54b in the direction of arrow "H" until the light reaches the associated 57 beneath light pipe 54b. The light moving between LED 55, light pipe 54a, light pipe 54b and sensor 57 serves two purposes. If the light travelling in the direction of arrow "F" strikes film 16d extending above the opening 42n to any particular compartment 16c, then that information is fed back to the microcontroller 44f. Microcontroller 44f may subsequently make the determination that the associated dosette 17 is unopened and therefore medication "P" is still retained therein. If the light fails to strike any film 16d then the information fed back to the microcontroller 44f may result in the determination that the film 16d has been removed and that the medication "P" has therefore likely been removed from compartment 16c. (This may be verified by data fed to microcontroller 44f by sensors 48, 52.)

Furthermore, if the sensor 57 is not simply a light sensor but is additionally or alternatively a color sensor, then microcontroller 44f may be programmed to determine whether a color of light reflected by film 16d and received by sensor 57 matches a programmed color film that should be associated with a particular receptacle 42j. In other words, sensor 57 may be used to determine if a color "A" of film 16d or a color "B" of film 16d, or a color "C" or "D" of film 16d is present at any particular receptacle 42j. If the color light detected by sensor 57 matches the programmed color film that should be on the dosette 17 in a particular receptacle 42j, then no warning will be issued to the patient or to a caregiver. However, if the color of light captured by sensor 57 is different to the color film that programming indicates should be in that particular receptacle 42j then an alert may be issued to the patient and/or caregiver to check the placement of the individual dosettes 17 in day module 14. If an alert is received then the patient or caregiver knows to make appropriate corrections by moving the individual dosettes. If, for example, a first color "A" of film 16d should be on the dosette 17 in a particular receptacle 42j and the first color light "A" is reflected into light pipe 54b and captured by the associated sensor 57; then no alert will be issued by day module 14. However, if a second color "B" of film 16d is actually detected on the dosette 17 in a particular receptacle 42j, then the light received by light pipe 54b and captured by sensor 57 will not match the color light that should be captured by that sensor 57. In this instance, day module 14 will issue an alert to the user to indicate that the particular dosette 17 has been loaded into the incorrect receptacle 42j. The issued alert may take any one of a number of forms including but not limited to flashing lights, audible sounds, displays of a messages on a display screen 56 on day module 14, and/or sending a text or email alert to a smart phone or other electronic device. The patient or caregiver will then be able to rearrange the loaded dosettes 17 into the correct compartments so that the correct dose of medication "P" is positioned to be removed at the correct, predetermined time of day. This system helps ensure that the patient will not take the wrong dose of medication at the wrong time of day.

Day module 14 may also include one or more Indicators 58 (FIG. 15) provided on an exterior surface of cover 42g in order to identify the time of day at which medication should be taken. Secondary indicators 60 (FIGS. 4 and 8) may also be provided on top wall 42e. Indicators 58, 60 may be utilized by the patient or a caregiver when loading individual dosettes 17 into receptacles 42j of day module 14. The user may visually check the column on the blister pack 16 from which they are detaching an individual dosette 17 and ensure that the indicator 22 at the top of that column is the same as the indicator 58 on the cover 42g and as the secondary indicator 60 on top wall 42e. The user may also utilize the colored film 16d on the detached dosette 17 by visually comparing that color of film with the color film 16d on the appropriate column on blister pack 16 to make sure they are loading the correct dosette 17 into the correct location on day module 14. As a further safety measure, light emitted and received by light pipes 54 as described above may also be used to verify that the correctly colored dosette 17 has been loaded into the appropriate and correct receptacle 42j and to subsequently to determine if medication in those dosettes has been taken as described above.

In other instances, light pipes, LEDs and sensors similar to light pipes 54, LEDs 55 and sensors 57 may additionally be provided at one end of a column of receptacles 20a on wall 20. These additional light pipes, LEDs and sensors may be utilized to determine the color of film 16d on a column of dosettes 17 in a particular position on blister pack 16. That gathered information may be compared (by the microcontroller 38) with the color of film 16d on a dosette 17 located in a corresponding receptacle 42j on day module 14 as determined by light pipes 54, LEDs 55 and sensors 57. A comparison will be made by microcontroller 38 between the color of film 16d in one or more columns of blister pack 16 and the color of film 16d detected in the individual dosettes 17 in each receptacle 42j of day module 14. If a discrepancy is detected between the color film in any column of base module 12 and the associated receptacle of the day module 14, then an alert will be issued to the patient and/or caregiver. The patient or caregiver may then make appropriate corrections. This comparison may be automatically initiated by the closing of cover 42g or may be purposefully initiated by the user after loading day module 14.

Sensors 48 and 52 in combination with light pipes 54 may be used to verify if film 16d has been removed from a dosette 17 in day module 14 but some or all of the medication "P" remains within the required dosette 17 for a preset period of time. If this is the case the determination is made by the programming of microcontroller 44f that the patient has overlooked removing some or all of the medication "P" and issues an alert.

It will be understood that the activation of light pipes 54 to determine correspondence between day module dosettes 17 and the dosettes in blister pack 16 does not need to occur on a continuous basis as this may be a drain on the power of pill box 10. Instead, in order to reduce power consumption, the detection (i.e., activation of light pipes 54) may occur at preprogrammed intervals.

As shown in FIG. 4, cover 42g may also include a notched region 42p and a window 42q. Notched region 42p and window 42q permit components such as control buttons 62 and digital display 56 to be visible and operable when cover 42g is in the closed position.

In order to interlockingly engage day module 14 with base module 12, a locking mechanism is provided. This locking mechanism may be located partially on day module 14 and partially on housing 18. As illustrated in the attached figures, such as FIGS. 8, 15 & 16, the locking mechanism may comprise one or more grooves 64 defined in at least one of front and rear walls 42a, 42b of housing 42 of day module 14; and complementary ribs 66 provided on interior faces of first and second arms 19a, 19b of housing 18. Ribs 66 may be interlocking received within grooves 64 when day housing 14 is slidingly inserted into recess 18h defined between first and second arms 19a, 19b in the direction of arrow "P" (FIG. 8). It will be understood that ribs 66 may, alternatively, be provided on housing 42 and that grooves 64 may be provided on housing 42; or that any other type of locking mechanism may be utilized to detachably secure day module 14 and base module 14 together.)

The electronic components within day module 14 (e.g. the microcontroller 44f and PCB 44 with sensors 48, 52 etc.) may also be operatively engaged with the electronic components (e.g. the microcontroller 38 and PCB 28 with sensors 34, 36) within base module 12 via mating electric connectors 68 and 70. (FIGS. 8-10). The mating engagement of connectors 68, 70 and interlocking grooves and ribs 66, 68, may assist in keeping day module 14 and base module 12 engaged with each other together. When day module 14 and base module 12 are engaged, then microcontroller 38 may control most or all of the functions of the entire box 10. When day module 14 is disengaged from base module 12, then the microcontroller 44f in day module 14 may control all of the functions, including reminder functions, of day module 14; and microcontroller 38 in base module 12 may control all of the functions, including reminder functions, of base module 12.

The electronic reminder system 10 disclosed herein functions in much the same manner as the electronic reminder systems described in the related applications U.S. patent application Ser. No. 14/858,041 filed Sep. 19, 2015 and U.S. patent application Ser. No. 13/965,966, filed Aug. 13, 2013, the disclosures of which have by incorporated herein by reference.

Additionally, microcontrollers in day module 14 and base module 12 may be programmed to include a unique internal electronic serial number. Day module 14 reads and records the base module's serial number when base and day modules 12, 14 are electronically connected together. The reading and recording of the serial number may particularly occur when the two modules are engaged and while downloading a new electronic reminder schedule. In the event that day unit 14 is disengaged from base module 12 and is later reconnected thereto, day module 14 reads the base module's internal electronic serial number and verifies that number with the previously recorded serial number. If the serial number of base module 12 does not match the serial number recorded by day module 14 during the download, the day module 14 may an alarm and may display an error message. It will be understood that the base module 12 may record the serial number of day module 14 during the time the base and day modules are engaged and if the modules 12, 14 are later disengaged and then reengaged, the base module 12 may perform the steps of verifying that the correct day module 14 has been docked therewith. If the serial number of day module 14 does not match the serial number recorded by base module 12 then an alarm or alert may be issued by base module 12 (and/or day module 14). In an environment such as a hospital where there may be multiple day and base modules in circulation, this system of cross-matching serial numbers will aid in preventing the wrong day module 14 and base module 12 from being engaged with each other by mistake.

In the foregoing description, certain terms have been used for brevity, clearness, and understanding. No unnecessary limitations are to be implied therefrom beyond the requirement of the prior art because such terms are used for descriptive purposes and are intended to be broadly construed.

Moreover, the description and illustration set out herein are an example and the invention is not limited to the exact details shown or described.

The invention claimed is:

1. An electronic pill box comprising:
a base module adapted to hold a blister pack comprising a plurality of dosettes each pre-loaded with a quantity of medication;
a day module engageable with the base module and being selectively disengageable therefrom, said day module being adapted to receive one or more dosettes detached from the blister pack; and
a first electronic reminder system provided in the base module or the day module, said first electronic reminder system being operable to remind a patient to remove a dose of medication from the pill box at a pre-determined time.

2. The electronic pill box as defined in claim 1, further comprising:
a second electronic reminder system provided in the other of the base module or the day module; said second electronic reminder system being operable to remind a patient to remove a dose of medication from the pill box at a pre-determined time.

3. The electronic pill box as defined in claim 2, wherein the first electronic reminder system is operable in the base module and the second electronic reminder system is operable in the day module when the day module is disengaged from the base module.

4. The electronic pill box as defined in claim 3, wherein each of the first and second electronic reminder systems includes a microcontroller; and the microcontrollers in the base module and day module are programmed to follow a same reminder schedule for a patient.

5. The electronic pill box as defined in claim 1, wherein the base module comprises:
a first plurality of receptacles each adapted to receive one of a plurality of dosettes of the pre-loaded blister pack; wherein each receptacle has a bottom wall with side walls extending upwardly therefrom; and
a capacitance sensor is spaced a distance below the bottom wall of each of the first plurality of receptacles.

6. The electronic pill box as defined in claim 5, wherein the base module further comprises:
a second capacitance sensor spaced a distance laterally from one or more of the side walls of each of the first plurality of receptacles.

7. The electronic pill box as defined in claim 5, wherein the day module comprises:

a second plurality of receptacles each adapted to receive a single dosette detached from the pre-loaded blister pack; wherein each of the second plurality of receptacles in the day module includes a bottom wall with side walls extending upwardly therefrom;

a capacitance sensor spaced a distance below the bottom wall of each of the second plurality of receptacles.

8. The electronic pill box as defined in claim 7, wherein the base module further comprises:

a second capacitance sensor spaced a distance laterally from one or more side walls of each of the second plurality of receptacles.

9. The electronic pill box as defined in claim 7, wherein together the first plurality of receptacles holds sufficient medication for one month and the second plurality of receptacles holds sufficient medication for one day.

10. In combination, an electronic pill box comprising:

a base module having a first plurality of receptacles therein;

a day module engageable with the base module and being selectively disengageable therefrom; said day module having a second plurality of receptacles therein, where the second plurality of receptacles is less than the first plurality of receptacles;

a first electronic reminder system provided in the base module or the day module, said first electronic reminder system being operable to remind a patient to remove a dose of medication from the pill box at a pre-determined time; and a blister pack comprising a first plurality of dosettes joined together in side-by-side relationship, each dosette being pre-loaded with a dose of medication; and wherein the blister pack is removably engaged with the base module in such a way that each dosette is received within a different one of the first plurality of receptacles of the base module.

11. The combination as defined in claim 10, wherein a second plurality of dosettes are separated from the blister pack and are each engaged in a different one of the second plurality of receptacles in the day module.

12. The combination as defined in claim 10, wherein the first electronic reminder system includes a printed circuit board (PCB) including a plurality of capacitance sensors provided on a substrate; and each sensor of a first group of the plurality of capacitance sensors is positioned a distance beneath a bottom wall of a different one of the receptacles in the base module or in the day module.

13. The combination as defined in claim 12, wherein each sensor of a second group of the plurality of capacitance sensors is positioned a distance from a side wall of a different one of the receptacles in the base module or in the day module.

14. The combination as defined in claim 10, further comprising a microcontroller and an accelerometer provided in one of both of the base module and the day module, said microcontroller and accelerometer being operatively engaged with each other.

15. The combination as defined in claim 10, wherein the blister pack includes a film that extends across the first plurality of dosettes, and wherein the film is color-coded for a time of day when a dose of medication is to be taken from each of the dosettes of the blister pack.

16. The combination as defined in claim 15, wherein the film is color-coded in at least two different colors, wherein a first color represents a first time of day a dose of medication is to be taken from a first group of dosettes; and a second color represents a second time of day a dose of medication is to be taken from a second group of dosettes.

17. The combination as defined in claim 15, wherein the day module further comprises:

a top wall defining the second plurality of receptacles therein;

an opening defined in the top wall proximate one end of each of the receptacles;

a first light pipe and a second light pipe positioned to terminate proximate each opening; the first and second light pipes extending inwardly from the opening and into a cavity defined beneath the top wall;

a light source positioned proximate an end of the first light pipe remote from the opening;

a light sensor positioned proximate an end of the second light pipe remote from the opening; wherein light from the light source travels along the first light pipe, is reflected off a portion of the film on a dosette engaged in an associated receptacle, travels along the second light pipe and is received by the light sensor.

18. The combination as defined in claim 17, wherein the portion of the dosette in the associated receptacle extends over the opening and includes a region of the colored film.

19. A method of using an electronic pill box comprising:

providing an electronic pill box comprising a base module, a day module engageable with the base module and being selectively disengageable therefrom, a first electronic reminder system provided in the base module, a second electronic reminder system provided in the day module; and a blister pack pre-loaded with a plurality of doses of medication, each of said doses being retained in a dosette sealed by way of a colored film;

detaching one or more individual dosettes from the blister pack;

loading each detached dosette into a different one of a plurality of receptacles in the day module;

activating a light source positioned adjacent each receptacle;

causing light to travel along a first light pipe positioned proximate the light source;

reflecting the light from the colored film of the dosette loaded into a particular receptacle;

causing the reflected light to travel along a second light pipe; and detecting a color of the light traveling along the second light pipe by way of a color sensor.

20. The method as defined in claim 19, further comprising:

linking the color sensor to a microcontroller provided in the day module or the base module;

transferring data regarding the detected color of the light to the microcontroller comparing, in the microcontroller, the detected color of the light with a set of pre-determined colors to be associated with each of the receptacles in the day module; and issuing an alarm to a patient if the detected color of the light is different from a pre-determined color for a specific one of the receptacles.

* * * * *